United States Patent
Nuzzo et al.

(10) Patent No.: US 7,909,971 B2
(45) Date of Patent: Mar. 22, 2011

(54) MICROFLUIDIC ELECTROCHEMICAL REACTORS

(75) Inventors: Ralph G. Nuzzo, Champaign, IL (US); Svetlana M. Mitrovski, Urbana, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 1779 days.

(21) Appl. No.: 11/074,596

(22) Filed: Mar. 8, 2005

(65) Prior Publication Data

US 2005/0233198 A1 Oct. 20, 2005

Related U.S. Application Data

(60) Provisional application No. 60/551,276, filed on Mar. 8, 2004.

(51) Int. Cl.
 *G01N 27/404* (2006.01)
 *H01M 8/08* (2006.01)
(52) U.S. Cl. .......................... 204/432; 204/600; 429/34
(58) Field of Classification Search .................. 204/400, 204/431, 432, 450, 600; 429/34
See application file for complete search history.

(56) References Cited

U.S. PATENT DOCUMENTS

| | | | |
|---|---|---|---|
| 3,764,248 A | 10/1973 | Hall | |
| 4,126,292 A | 11/1978 | Saeki et al. | |
| 5,071,597 A | 12/1991 | D'Amato et al. | |
| 5,502,144 A | 3/1996 | Kuo et al. | |
| 5,534,609 A | 7/1996 | Lewis et al. | |
| 5,538,674 A | 7/1996 | Nisper et al. | |
| 5,618,903 A | 4/1997 | Hoxmeier et al. | |
| 5,637,668 A | 6/1997 | Graiver et al. | |
| 5,661,092 A | 8/1997 | Koberstein et al. | |
| 5,670,598 A | 9/1997 | Leir et al. | |
| 5,676,983 A | 10/1997 | Bacher et al. | |
| 5,741,859 A | 4/1998 | Saxena et al. | |
| 5,744,541 A | 4/1998 | Sawaguchi et al. | |
| 5,795,519 A | 8/1998 | Bacher et al. | |
| 5,932,649 A | 8/1999 | Hergenrother et al. | |
| 5,932,677 A | 8/1999 | Hoover et al. | |
| 6,007,914 A | 12/1999 | Joseph et al. | |
| 6,013,711 A | 1/2000 | Lewis et al. | |
| 6,013,715 A | 1/2000 | Gornawicz et al. | |
| 6,033,202 A | 3/2000 | Bao et al. | |

(Continued)

FOREIGN PATENT DOCUMENTS

DE 101 55 349 A1 5/2003

(Continued)

OTHER PUBLICATIONS

Choban, E.R., et al., "Microfluidic fuel cells that lack a PEM", 40th Conference on Power Sources, pp. 317-320, (2002).

(Continued)

*Primary Examiner* — Kaj K Olsen
(74) *Attorney, Agent, or Firm* — Evan Law Group LLC

(57) ABSTRACT

A microfluidic electrochemical reactor includes an electrode and one or more microfluidic channels on the electrode, where the microfluidic channels are covered with a membrane containing a gas permeable polymer. The distance between the electrode and the membrane is less than 500 micrometers. The microfluidic electrochemical reactor can provide for increased reaction rates in electrochemical reactions using a gaseous reactant, as compared to conventional electrochemical cells. Microfluidic electrochemical reactors can be incorporated into devices for applications such as fuel cells, electrochemical analysis, microfluidic actuation, pH gradient formation.

19 Claims, 22 Drawing Sheets

U.S. PATENT DOCUMENTS

| | | | |
|---|---|---|---|
| 6,072,011 A | 6/2000 | Hoover | |
| 6,090,902 A | 7/2000 | Kuo et al. | |
| 6,103,837 A | 8/2000 | Hiiro et al. | |
| 6,124,411 A | 9/2000 | Matyjaszewski et al. | |
| 6,136,926 A | 10/2000 | Raetzsch et al. | |
| 6,153,691 A | 11/2000 | Gomowicz et al. | |
| 6,235,863 B1 | 5/2001 | Hoxmeier | |
| 6,339,131 B1 | 1/2002 | Cella et al. | |
| 6,344,521 B1 | 2/2002 | Schwindeman et al. | |
| 6,362,288 B1 | 3/2002 | Brewer et al. | |
| 6,363,183 B1 | 3/2002 | Koh | |
| 6,372,532 B2 | 4/2002 | Bao et al. | |
| 6,403,710 B1 | 6/2002 | Ahmed et al. | |
| 6,407,193 B1 | 6/2002 | Hiiro et al. | |
| 6,663,820 B2 | 12/2003 | Arias et al. | |
| 6,805,809 B2 | 10/2004 | Nuzzo et al. | |
| 6,835,293 B2 * | 12/2004 | Gerlach et al. | 204/600 |
| 2002/0054862 A1 | 5/2002 | Perron et al. | |
| 2002/0179448 A1 * | 12/2002 | Lauks | 204/600 |
| 2003/0013046 A1 | 1/2003 | Fonash et al. | |
| 2003/0024632 A1 | 2/2003 | Hahn et al. | |
| 2003/0127333 A1 * | 7/2003 | Lauks et al. | 204/600 |
| 2004/0040653 A1 | 3/2004 | Nuzzo et al. | |

FOREIGN PATENT DOCUMENTS

| | | |
|---|---|---|
| WO | WO 01/18857 A1 | 3/2001 |
| WO | WO 03/002247 A1 | 1/2003 |
| WO | WO 2004/021084 A2 | 3/2004 |

OTHER PUBLICATIONS

Clark, L.C., "Monitor and control of blood and tissue oxygen tensions", Trans. Am. Soc. Artificial Internal Organs, vol. 2, pp. 41-57, (1956).

Allcock, H.R., et al., "Contemporary Polymer Chemistry—Second Edition", published by Prentice-Hall Inc., New Jersey, pp. 146-149, (1990).

Deng, T., et al., "Using patterns in microfiche as photomasks in 10-μm-scale microfabrication", Langmuir, vol. 15, No. 19, pp. 6575-6581, (1999).

Deng, T., et al., "Prototyping of masks, masters, and stamps/molds for soft lithography using an office printer and photographic reduction", Analytical Chemistry, vol. 72, No. 14, pp. 3176-3180, (2000).

Douki, K., et al., "High-Performance 193-nm positive resist using alternating polymer system of functionalized cyclic olefins / maleic anhydride", Advances in Resist Technology and Processing XVII, Proceedings of SPIE, vol. 3999, pp. 1128-1133, (2000).

International Search Report for PCT application No. PCT/US03/26751 dated Feb. 13, 2004.

Ouyang, M., et al., "Conversion of some siloxane polymers to silicon oxide by UV/Ozone photochemical processes", Chem. Mater., vol. 12, No. 6, pp. 1591-1596, (2000).

Stevens, M.P., "Polymer Chemistry: an introduction—Third Edition", published by Oxford University Press, New York, pp. 276-279, (1999).

Xia, Y., et al., "Soft Lithography", Annu. Rev. Mater. Sci., vol. 28, pp. 153-184, (1998).

Menard, E., et al., "A printable form of silicon for high performance thin film transistors on plastic substrates", Applied Physics Letters, vol. 84, No. 26, pp. 5398-5400, (2004).

Wallraff, G.M., et al., "Lithographic imaging techniques for the formation of nanoscopic features", Chemical Reviews, vol. 99, No. 7, pp. 1801-1821, (1999).

Reichmanis, E., et al., "Organic materials challenges for 193 nm imaging", Accounts of Chemical Research, vol. 32, No. 8, pp. 659-667, (1999).

Houlihan, F.M., et al., "Retrospective of work at Bell Laboratories on the effect of fluorine substitution on the properties of photoacid generators", Journal of Fluorine Chemistry, vol. 122, pp. 47-55, (2003).

Lee, K., et al., "Photolithographic technique for direct photochemical modification and chemical micropatterning of surfaces", Langmuir, vol. 20, No. 5, pp. 1812-1818, (2004).

Childs, W.R., et al., "Decal transfer microlithography: A new soft-lithographic patterning method", Journal of the American Chemical Society, vol. 124, No. 45, pp. 13583-13596, (2002).

Chen, T., et al., "A miniature biofuel cell", J. Am. Chem. Soc., vol. 123, No. 35, pp. 8630-8631, (2001).

Ehrfeld, W., "Electrochemistry and Microsystems", Electrochimica Acta, vol. 48, pp. 2857-2868, (2003).

International Search Report dated Sep. 26, 2006 for PCT application No. PCT/US2005/007567.

Katz, E., et al., "A biofuel cell with electrochemically switchable and tunable power output", J. Am. Chem. Soc., vol. 125, No. 22, pp. 6803-6813, (2003).

Lawrence, N.S., et al., "A thin-layer amperometric sensor for hydrogen sulfide: The use of microelectrodes to achieve a membrane-independent response for clark-type sensors", Analytical Chemistry, vol. 75, No. 10, pp. 2499-2503, (2003).

Mancy, K.H., et al., "A galvanic cell oxygen analyzer", Journal of Electroanalytical Chemistry, vol. 4, pp. 65-92, (1962).

Mano, N., et al., "A miniature biofuel cell operating in a physiological buffer", J. Am. Chem. Soc., vol. 124, No. 44, pp. 12962-12963, (2002).

Mano, N., et al., "Characteristics of a miniature compartment-less glucose-$O_2$ biofuel cell and its operation in a living plant", J. Am. Chem. Soc., vol. 125, No. 21, pp. 6588-6594, (2003).

Martin, M.M., et al., "The pH dependence of fluorescein fluorescence", Journal of Luminescence, vol. 10, pp. 381-390, (1975).

Palmore, G.T.R., et al., "Electro-enzymatic reduction of dioxygen to water in the cathode compartment of a biofuel cell", Journal of Electroanalytical Chemistry, vol. 464, pp. 110-117, (1999).

Pijanowska, D.G., et al., "A flow-through amperometric sensor for micro-analytical systems", Sensors and Actuators B, vol. 91, pp. 98-102, (2003).

Xia, Y., et al., "Soft lithography", Angew. Chem. Int. Ed., vol. 37, pp. 550-575, (1998).

* cited by examiner

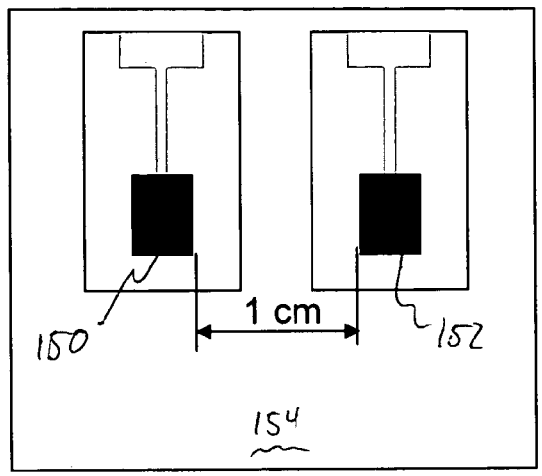
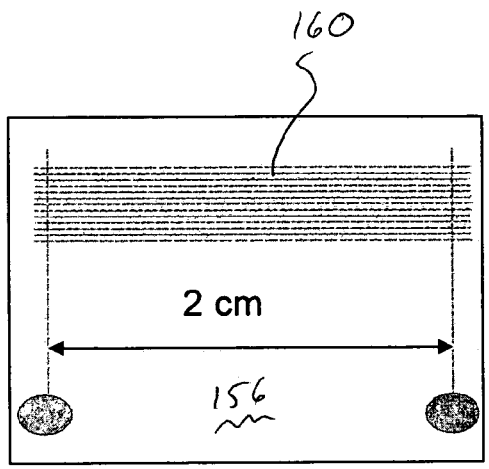
FIG. 7A
FIG. 7B
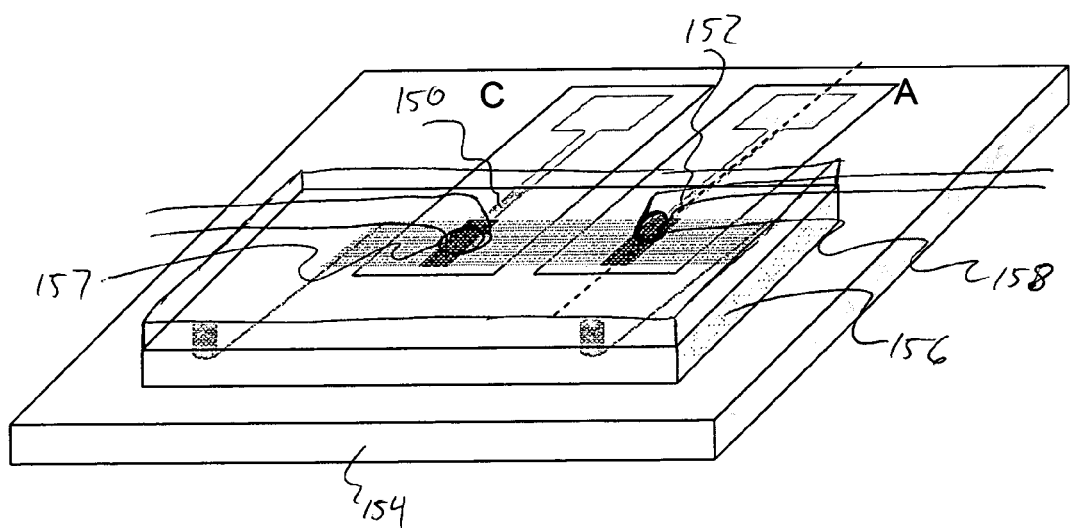
FIG. 7C

O₂        Air

MICROFLUIDIC ELECTROCHEMICAL REACTORS

REFERENCE TO RELATED APPLICATIONS

This application claims the benefit of U.S. Provisional Application No. 60/551,276 entitled "Microfluidic Electrochemical Reactors" filed Mar. 8, 2004, which is incorporated by reference in its entirety.

FEDERALLY SPONSORED RESEARCH OR DEVELOPMENT

The subject matter of this application was in part funded by the Department of Energy (DOE Grant no. DEFG02-91 ER45439). The government may have certain rights in this invention.

BACKGROUND

Microelectrochemical reactors increasingly have been studied for use in a variety of applications. In analytical applications, microelectrochemical reactors can provide for measurement of small quantities or concentrations of an analyte, as long as the analyte can undergo an electrochemical reaction. In power generation applications, microelectrochemical reactors can be used to construct batteries or fuel cells that are extremely small and light weight. In other applications, microelectrochemical reactors can be used to perform microchemical synthesis, to perform microfluidic pumping, or to pattern a surface.

For example, microelectrochemical sensors have been used for applications ranging from the detection of glucose by diabetes patients to the detection of small amounts of gas in liquid or atmospheric samples. Conventional gas sensing systems are typically based on amperometric Clark sensors having a chamber in which an electrolyte and microelectrodes are housed. A gas permeable membrane is used to separate the electrolyte and electrodes from the outside sample. The purpose of the membrane is to enhance the sensitivity and to shield the electrode from interfering species. However, the performance of these sensors can be limited by the diffusion of the gaseous analyte through both the membrane and the electrolyte. Typically, these sensor systems are less sensitive than a bare platinum electrode under a controlled environment.

In another example, fuel cells are under intense development as potential alternative energy sources that are lightweight and compact and that can provide high power densities. When oxygen is consumed by a fuel cell, the activity of the cathode where the oxygen is reduced can be particularly degraded by the concentration polarization associated with the mass transport resistance within the fuel cell. It is believed that minimizing this resistance can provide an improvement in power density operation of the fuel cell. In polymer electrolyte membrane (PEM) fuel cells, platinum is used as the cathode, and a perfluorosulfonic acid polymer membrane is the solid electrolyte. Although the polymer membrane can minimize the degradation of the cathode activity by suppressing the crossover of the anode fuel to the cathode, the lifetime of the PEM fuel cell typically is limited by the dehydration of the polymer membrane, due to the high temperatures developed during operation of the fuel cell. Even without the constraints of a membrane, the performance of a fuel cell typically will be limited by the amount of dissolved oxygen in the liquid electrolyte.

In another example, electrochemical reactions have been used to provide for pumping liquids within microfluidic systems for applications such as drug delivery, chemical blood analysis and flow cytometry. Pumping systems for microfluidic devices typically have been based on either electrokinetic or hydrodynamic principles. Electrokinetically induced pumping requires high voltages of approximately 30 kV, and the electrical currents generated can cause water electrolysis at the electrodes, resulting in significant Joule heating and generation of bubbles. Hydrodynamic pumping requires the use of auxiliary, macroscopic components such as syringe pumps, which are complicated to integrate with the microfluidic system and are not typically disposable. However, a microelectrochemical approach to microfluidic pumping involves the generation of a surface pressure gradient between two microelectrodes and requires only low voltages. The formation of a surface active species at one electrode and its consumption at the other electrode can provide sufficient surface pressure to move droplets of organic liquids through a microfluidic network. A disadvantage of the typical microelectrochemical approach is the requirement for a redox active surfactant in the system, which may be incompatible with the fluid of interest or with the surface properties of the network material.

It is thus desirable to provide microelectrochemical reactors having improved reactivity for the reactions occurring at the microelectrodes. It is also desirable to provide microelectrochemical devices with improved performance, such as sensors having improved sensitivity, fuel cells providing increased power and current densities, and microfluidic pumps having a simpler design and a more effective performance.

SUMMARY

In one aspect, the invention provides an electrochemical reactor that includes an electrode, at least one microfluidic channel on the electrode, and a membrane comprising a gas permeable polymer on the microfluidic channel. The distance between the electrode and the membrane is less than 500 microns.

In another aspect of the invention, there is an electrochemical reactor that includes an electrode, and at least two microfluidic channels on the electrode. The microfluidic channels include a top membrane including a gas permeable polymer and having a thickness from 1 micron to 2 millimeters, side walls extending between the electrode and the membrane, a distance between the electrode and the membrane less than 500 microns, a distance between the side walls from 1 micron to 1 millimeter, and a separation between the channels from 1 micron to 1 millimeter.

In yet another aspect of the invention, there is an electrochemical device that includes an electrochemical reactor and a second electrode in electrochemical communication with the electrode of the reactor.

In yet another aspect of the invention, there is a microfluidic electrochemical sensor that includes an electrochemical reactor, where the electrode of the reactor is a working electrode, and a counter electrode in electrochemical communication with the working electrode.

In yet another aspect of the invention, there is a microfluidic actuator that includes an electrochemical reactor and a second electrode in electrochemical communication with the electrode of the reactor through the at least one microfluidic channel, where the application of an electric potential to the electrode of the reactor causes a net flow of electrolyte along the channel.

In yet another aspect of the invention, there is a microfluidic fuel cell that includes a first electrochemical reactor, a second electrochemical reactor, in electrochemical communication with the first electrochemical reactor, and including a second electrode, at least one microfluidic channel on the second electrode and a membrane comprising a gas permeable polymer on the microfluidic channel, where the distance between the electrode and the membrane is less than 500 microns. The microfluidic fuel cell further includes an inlet for an oxidant to the first electrochemical reactor, and an inlet for a reductant to the second electrochemical reactor.

In yet another aspect of the invention, there is a method of making a microfluidic electrochemical reactor that includes forming a gas permeable polymer layer comprising a first side and a second side, and contacting the first side of the gas permeable polymer layer with a substrate and an electrode on the substrate. The first side of the gas permeable polymer layer defines interconnected channels, and the second side of the gas permeable polymer layer includes a membrane covering the interconnected channels. The channels, the portions of the electrode and substrate that are exposed to the channels, and the membrane covering the channels form a microfluidic network.

In yet another aspect of the invention, there is an electrochemical reactor, comprising a substrate comprising a surface; an electrode on a portion of the substrate surface; a portion of at least one microfluidic channel on the electrode; a membrane comprising a gas permeable polymer on the portion of the microfluidic channel; and an electrolyte in the microfluidic channel.

In another aspect of the invention, there is an electrochemical reactor, comprising a substrate comprising a surface; an electrode on a portion of the substrate surface; and portions of at least two microfluidic channels on the electrode. The portions of the microfluidic channels include a top membrane comprising a gas permeable polymer, the membrane having a thickness from about 1 micron to about 2 millimeters. The portions of the microfluidic channels include side walls extending between the electrode and the membrane. The portions of the microfluidic channels include a height, defined by the distance between the electrode and the membrane, from about 1 micron to about 500 microns. The portions of the microfluidic channels include a width between the side walls from about 1 micron to about 1 millimeter. The portions of the microfluidic channels include a separation between the portions of the channels from about 1 micron to about 1 millimeter. The portions of the microfluidic channels include an electrolyte in the portions of the microfluidic channels.

In yet another aspect of the invention, there is an electrochemical device, comprising a substrate comprising a surface; a first electrode on a portion of the substrate surface; a first portion of at least one microfluidic channel on the first electrode; a first membrane comprising a gas permeable polymer on the first portion of the microfluidic channel; an electrolyte in the microfluidic channel; and a second electrode in electrochemical communication with the first electrode.

In yet another aspect of the invention, there is a microfluidic electrochemical sensor, comprising a substrate comprising a surface; a working electrode on a portion of the substrate surface; a portion of at least one microfluidic channel on the working electrode; a membrane comprising a gas permeable polymer on the portion of the microfluidic channel; an electrolyte in the microfluidic channel; and a counter electrode in electrochemical communication with the working electrode.

In yet another aspect of the invention, there is provided a microfluidic actuator, comprising a substrate comprising a surface; a first electrode on a portion of the substrate surface; a first portion of at least one microfluidic channel on the first electrode; a first membrane comprising a gas permeable polymer on the first portion of the microfluidic channel; an electrolyte in the microfluidic channel; and a second electrode in electrochemical communication with the first electrode. The application of an electric potential to the first electrode causes a pH gradient to form between the first electrode and the second electrode, such that there is a net flow of electrolyte along the gradient.

In yet another aspect of the invention, there is a microfluidic fuel cell, comprising a substrate comprising a surface; a cathode on a first portion of the substrate surface; an anode on a second portion of the substrate surface; at least one microfluidic channel on the substrate. A first portion of the microfluidic channel is on the cathode, and a first membrane comprising a gas permeable polymer is on the first portion of the microfluidic channel. A second portion of the microfluidic channel is on the anode, and a second membrane comprising a gas permeable polymer is on the second portion of the microfluidic channel; an electrolyte in the microfluidic channel; an inlet for an oxidant on the first membrane; and an inlet for a reductant on the second membrane.

In yet another aspect of the invention, there is provided a method of making a microfluidic electrochemical reactor, comprising forming an electrode in a pattern on a substrate; forming a gas permeable polymer layer comprising a first side and a second side, the first side defining interconnected channels and the second side comprising a membrane covering the interconnected channels; and contacting the first side of the gas permeable polymer layer with the electrode and the substrate. The channels, the portions of the electrode and substrate that are exposed to the channels, and the membrane covering the channels form a microfluidic network.

The scope of the present invention is defined solely by the appended claims and is not affected by the statements within this summary.

BRIEF DESCRIPTION OF THE DRAWINGS

Many of the features and dimensions portrayed in the drawings, and in particular the presentation of layer thicknesses and the like, and the spacing there between, have been somewhat exaggerated for the sake of illustration and clarity.

FIGS. 7A-7C are schematic illustrations of a microfluidic fuel cell for use with either gaseous or liquid reductants, where 7A is a top view of the electrodes, 7B is a top view of a microfluidic network, and 7C is a perspective view of the assembled fuel cell;

DETAILED DESCRIPTION

A microfluidic electrochemical reactor includes an electrode and one or more microfluidic channels on the electrode, where the microfluidic channels are covered with a membrane containing a gas permeable polymer. The distance between the electrode and the membrane is less than 500 micrometers. The microfluidic electrochemical reactor can provide for increased reaction rates in electrochemical reactions using a gaseous reactant, as compared to conventional electrochemical cells. Current densities for such electrochemical reactions can be 3 to 5 times greater than those achieved by conventional electrochemical cells. Optimization of the microfluidic electrochemical reactor configuration can provide for current densities that are greater than those of conventional electrochemical cells by an order of magnitude.

Devices incorporating a microfluidic electrochemical reactor can provide for increased performance relative to devices that use conventional electrochemical cells. Fuel cells incorporating microfluidic electrochemical reactors at the anode and cathode can provide for improved power densities relative to other microfluidic fuel cells or to biofuel cells. An additional advantage of fuel cells incorporating microfluidic electrochemical reactors is that no pumps are needed to supply the reagent to the fuel cell, even when the fuel is a liquid such as formic acid or methanol. Microfluidic actuators incorporating microfluidic electrochemical reactors can provide for fluid flow at low applied voltage, such as from 0.1 to 1.0 volt. Chemical reactions can also be facilitated by microfluidic electrochemical reactors, particularly when the reactions are pH sensitive. The generation of pH changes and/or gradients by a microfluidic electrochemical reactor can provide useful features such as in situ reagent release and pH-related separations.

Components

Figure 1:
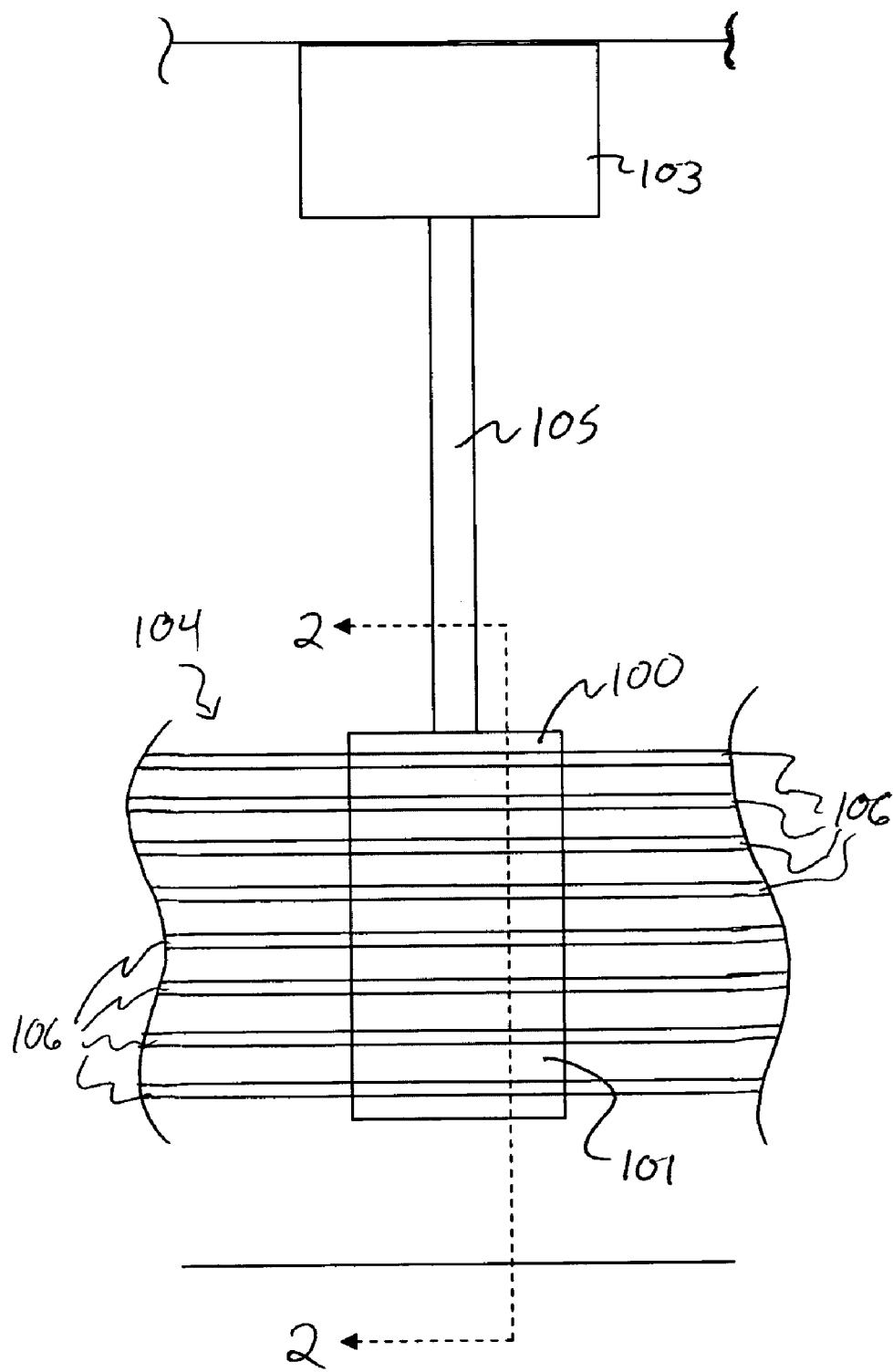
FIG. 1 is a schematic illustration of a top view of a microfluidic electrochemical reactor.
Figure 2:
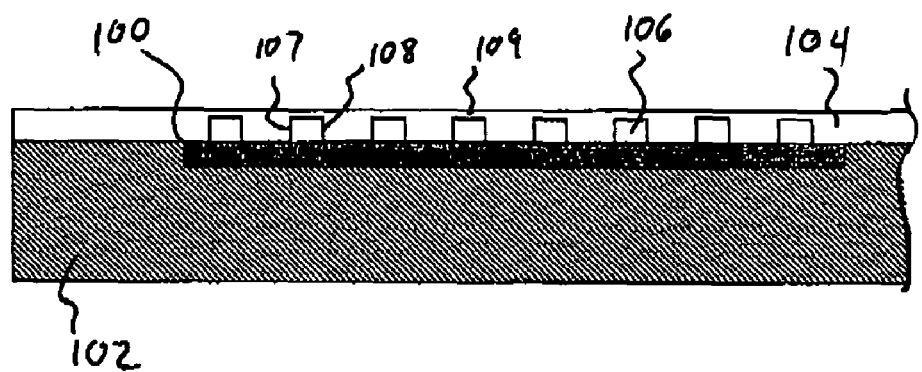
FIG. 2 is a schematic illustration of a cross-sectional view of the microfluidic electrochemical reactor taken along line 2-2 in FIG. 1.

An example of a microfluidic electrochemical reactor is shown schematically in FIGS. 1-2. Electrode 100 is on a substrate 102, and a microfluidic network 104 is on both the electrode and the substrate. The microfluidic network 104 contains one or more microfluidic channels 106. For rectangular channels as illustrated in the example of FIG. 2, an individual channel has walls 107 and 108 and a top membrane 109. The channels can be filled with a fluid, preferably with a liquid such as an electrolyte solution.

The term "microfluidic channel" is defined as an elongated structure through which fluid can flow, and containing features that are 1,000 micrometers (microns, abbreviated "µm") or smaller. In one example, a microfluidic channel can be a hollow cylinder having a diameter of 1,000 µm (1 millimeter (mm)) or smaller and a length of greater than 1 mm. In another example, a microfluidic channel can be a hollow rectangular prism having a width of 1 mm or smaller or a height of 1 mm or smaller, and having a length of greater than 1 mm. The term "microfluidic network" is defined as a structure of interconnected microfluidic channels.

The terms "microfluidic electrochemical reactor" and "microfluidic reactor," as used synonymously herein, are defined as an electrode covered with at least one microfluidic channel. The portions of exposed surface area of the electrode are in contact with any fluid that is present in the channel.

The terms "microfluidic electrochemical cell" and "microfluidic cell," as used synonymously herein, are defined as an electrochemical cell in which at least one of the electrodes in the cell is a microfluidic reactor.

The term "microfluidic electrochemical device" and microfluidic device," as used synonymously herein, are defined as a microfluidic electrochemical cell configured for a specific application. A microfluidic electrochemical cell may be configured for a variety of applications, including an electroanalytical cell, a fuel cell, a battery, a pH gradient generator, a fluid actuator and/or a microfluidic pump.

The electrode 100 can be any electrically conductive material, including metals, metal oxides, conductive polymers, and conductive carbon. Examples of conductive materials include a thin layer of a metal such as gold, silver, platinum, palladium, copper, tungsten, ruthenium or alloys of these metals with each other or with other metals, as well as a thin layer of conductive carbon powder. Preferably, the electrode is a thin film of a metal. As illustrated in the example of FIG. 1, the electrode 100 may be patterned to provide an active region 101, a lead attachment region 103 and a connection region 105 forming a conductive pathway between the active region and the lead attachment region. Preferably the connection region is completely covered. Although at least a portion of the lead attachment region may be uncovered, so as to allow the reactor to be electrically connected to other devices or equipment, the lead attachment region is not exposed to the electrochemical environment of the microfluidic network.

Figure 3:
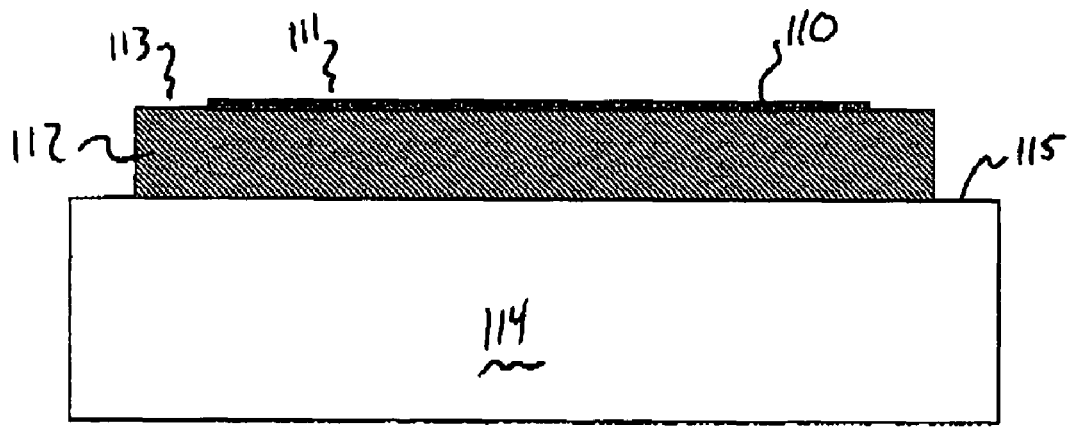
FIG. 3 is a cross-sectional view of a microfluidic electrochemical reactor.

The substrate 102 can be any material that can support the electrode and the microfluidic network and that does not interfere with the electrochemical properties of the electrode. The substrate can be flexible or rigid, and can thus provide for a microfluidic cell that is either flexible or rigid. Preferably the substrate is attached to the electrode and to the microfluidic network. Examples of substrate materials include polymers, ceramics, metals, and semiconductors. If the substrate is a polymer, the substrate may be the same material as the material used for the microfluidic network, or it may be a different material. The substrate may also contain more than one type of material. For example, referring to FIG. 3, the electrode 110 may be on a primary substrate 112, and the primary substrate can be attached to a secondary substrate 114. In this example, the secondary substrate may have a planar surface 115 onto which the primary substrate is attached, or the primary substrate may be fully or partially embedded into the secondary substrate. If the primary substrate is embedded into the secondary substrate, the surface 115 of the secondary substrate may be co-planar with the surface 113 of the primary substrate, or it may be co-planar with the surface 111 of the electrode.

The top membrane 109 may be made of a gas permeable polymer. The term "gas permeable polymer" is defined as any polymer that allows for permeation of one or more gaseous species through the polymer. The gaseous species may be present in a gaseous environment, or it may be dissolved in a liquid. The gaseous species may be a vaporized form of a substance that is normally a liquid at standard temperature and pressure. The ability of a substance to permeate through a material is quantified by the permeability coefficient (P), which is expressed in units of cubic centimeter-centimeter per cubic centimeter-second-Pascal ($cm^3$ $cm/cm^3$ s Pa), and is measured with respect to standard temperature and pressure ($0°$ C. and $1.013 \times 10^5$ Pa pressure). Preferably, the gas permeable polymer has a permeability coefficient P, at standard temperature and pressure, for at least one gas of at least $5 \times 10^{-13}$ $cm^3$ $cm/cm^3$ s Pa. More preferably, the gas permeable polymer has a permeability coefficient P, at standard temperature and pressure, for at least one gas of at least $10 \times 10^{-13}$ $cm^3$ $cm/cm^3$ s Pa. Even more preferably, the gas permeable polymer has a permeability coefficient P, at standard temperature and pressure, for at least one gas of at least $1 \times 10^{-10}$ $cm^3$ $cm/cm^3$ s Pa; even more preferably of at least $1 \times 10^{-8}$ $cm^3$ $cm/cm^3$ s Pa; even more preferably of at least $1 \times 10^{-6}$ $cm^3$ $cm/cm^3$ s Pa.

Examples of gases which can permeate through a gas permeable polymer include oxygen, hydrogen, nitrogen, nitrogen monoxide, carbon dioxide, carbon monoxide, hydrogen sulfide, water vapor, methane, ethane, propane, butane, fluorine, chlorine, and radon. Examples of gases which can permeate through a gas permeable polymer also include vapors of organic compounds including hydrocarbons, such as hexane, benzene and toluene; alcohols, such as methanol and ethanol; aldehydes such as formaldehyde; and acids such as formic acid and acetic acid. Preferably the gas permeable polymer has a permeability coefficient meeting the above values for oxygen, hydrogen, carbon dioxide and/or nitrogen monoxide. Preferably the polymer has a permeability coefficient meeting the above values for oxygen.

Examples of gas permeable polymers include polymers containing diene monomeric units, polypropylene, silicon-containing polymers and fluorinated polymers. Examples of polymers containing diene monomeric units include polyisoprene; polybutadiene; polychloroprene; styrenic block copolymers, such as styrene-butadiene-styrene, styrene-isoprene-styrene, and hydrogenated derivatives thereof; natural rubber; ethylene-propylene-diene copolymers (EPDM); and block copolymers containing these polymers, and copolymers containing repeat units derived from their corresponding monomers. Examples of fluorinated polymers include poly(tetrafluoroethylene) and fluorinated ethylpropylene.

Preferably the gas permeable polymer is a silicon-containing polymer. More preferably, the gas permeable polymer is a silicon-containing elastomer. The term "elastomer," as used herein, is defined as a polymer which can return to its initial dimensions when deformed by an external force. A polymer is considered an elastomer when it meets the following standard. A sample of the polymer in its solid state and having an initial linear dimension $D^o$ is subjected to a force such that the dimension is changed by 10%. Once the force is no longer applied, the dimension assumes a value of $D^e$, where $D^e = D^o \pm 0.01 D^o$.

The term "silicon-containing elastomer," as used herein, is an elastomer which contains silicon (Si) atoms. Examples of silicon-containing elastomers include, but are not limited to, polysiloxanes, such as poly(dimethyl siloxane), poly(methyl siloxane), partially alkylated poly(methyl siloxane), poly (alkyl methyl siloxane) and poly(phenyl methyl siloxane); block copolymers containing segments of a polysiloxane and another polymer; silicon-modified elastomers, such as silicon-modified natural rubber, silicon-modified polyolefins (including silicon-modified polyisoprene, silicon-modified polybutadiene, and silicon-modified polyisobutylene), silicon-modified polyimides, silicon-modified crosslinked phenol-formaldehyde resins (Si-modified NOVOLAC), and silicon-modified polyurethane elastomers. Silicon modification of elastomers may be carried out by reactions with silanes and siloxanes, including hydrosilation and condensation. Preferably the silicon-containing elastomer contains a polysiloxane. More preferably, the silicon-containing elastomer is poly (dimethyl siloxane), referred to as "PDMS."

Further examples of silicon-containing elastomers include block copolymers of polysiloxanes with other polymers. For example, block copolymers containing polysiloxanes may be formed with polyolefins such as polyethylene (U.S. Pat. No. 5,618,903), poly(isobutylene) (U.S. Pat. No. 5,741,859), polypropylene (U.S. Pat. No. 5,744,541), polystyrene and various polydienes (U.S. Pat. No. 5,932,649), and polyisoprene and polybutadiene (U.S. Pat. No. 6,362,288). In another example, block copolymers containing polysiloxanes may be formed with acrylates (U.S. Pat. No. 6,090,902), with a wide variety of polymers formed by polymerization of unsaturated monomers (U.S. Pat. No. 6,124,411), and with a variety of types of siloxanes (U.S. Pat. No. 5,637,668). In another example, block copolymers containing polysiloxanes may be formed with condensation polymers such as polycarbonates (U.S. Pat. No. 6,072,011) and poly(arylene ethers) (U.S. Pat. No. 6,339,131) and may also be formed with polyethers such as polyethylene oxide and polypropylene oxide (U.S. Pat. No. 6,013,711). Further examples of silicon-containing elastomers include copolymers containing polysiloxane repeat units in combination with polyester and/or polycarbonate repeat units (U.S. Pat. No. 6,407,193), and also include blends of polysiloxanes with polyamides (U.S. Pat. No. 6,344,521) and blends of polysiloxanes with polyolefins, polyurethanes, or styrenic polymers (U.S. Pat. No. 6,153,691). Further examples of silicon-containing elastomers include polymers modified to contain silicon by treatment with silane compounds (U.S. Pat. No. 6,136,926).

Structure and Properties

The general configuration of the microfluidic electrochemical reactor thus includes one or more microfluidic channels having a bottom wall defined by the electrode or the substrate, and having a top wall that is a membrane of a gas permeable polymer. The thickness of the electrolyte layer on the electrode is determined by the height of the channels of the microfluidic network. The height of the channels is the distance from the bottom wall (substrate or electrode) and the top wall. Preferably, the height of the channels is less than 500 microns. More preferably, the height of the channels is from 1 micron to 500 microns. More preferably, the height of the channels is from 10 microns to 300 microns, and even more preferably from 25 microns to 100 microns. The electroactive area of the electrode is the portion of the electrode that is exposed to the channels, and is determined by the width of the channels between the side walls. Preferably, the width of the channels is from 1 micron to 1 millimeter. More preferably, the width of the channels is from 10 microns to 500 microns, and even more preferably from 50 microns to 300 microns. Preferably, if more than one channel is present, the channels are separated by a distance from 1 micron to 1 millimeter. More preferably, the channels are separated by a distance from 10 microns to 500 microns, and even more preferably from 50 microns to 300 microns.

A microfluidic electrochemical reactor can provide for increased reaction rates at the electrode for reactions involving an electrolyte and a gas reactant. These increased reaction rates are in comparison to electrochemical cells having a bare electrode in a quiescent electrolyte solution and to electrochemical cells having an electrode coated with a gas permeable polymer. This configuration of electrode, microfluidic channel and gas permeable membrane can provide for increased amounts of reactants at the electrode, such that the reaction is not limited by the permeability through the electrolyte solution.

The increase in reaction rates is illustrated, for example, by the use of the microfluidic reactor in the oxygen reduction reaction (ORR):

$$O_2 + 2H_2O + 4e^- = 4OH^-.$$

It is believed that the mechanism of the ORR involves either direct production of hydroxide ($OH^-$) or a consecutive reaction pathway involving $H_2O_2$ as an intermediate. The products and intermediates of the ORR may reduce the reaction rate by acting as a barrier to the transport of oxygen to the surface of the electrode. For a standard electrochemical cell design, the reaction rate can be increased by introducing higher gas partial pressure, by mixing the electrolyte and/or by increasing the operating temperature.

Figure 4:
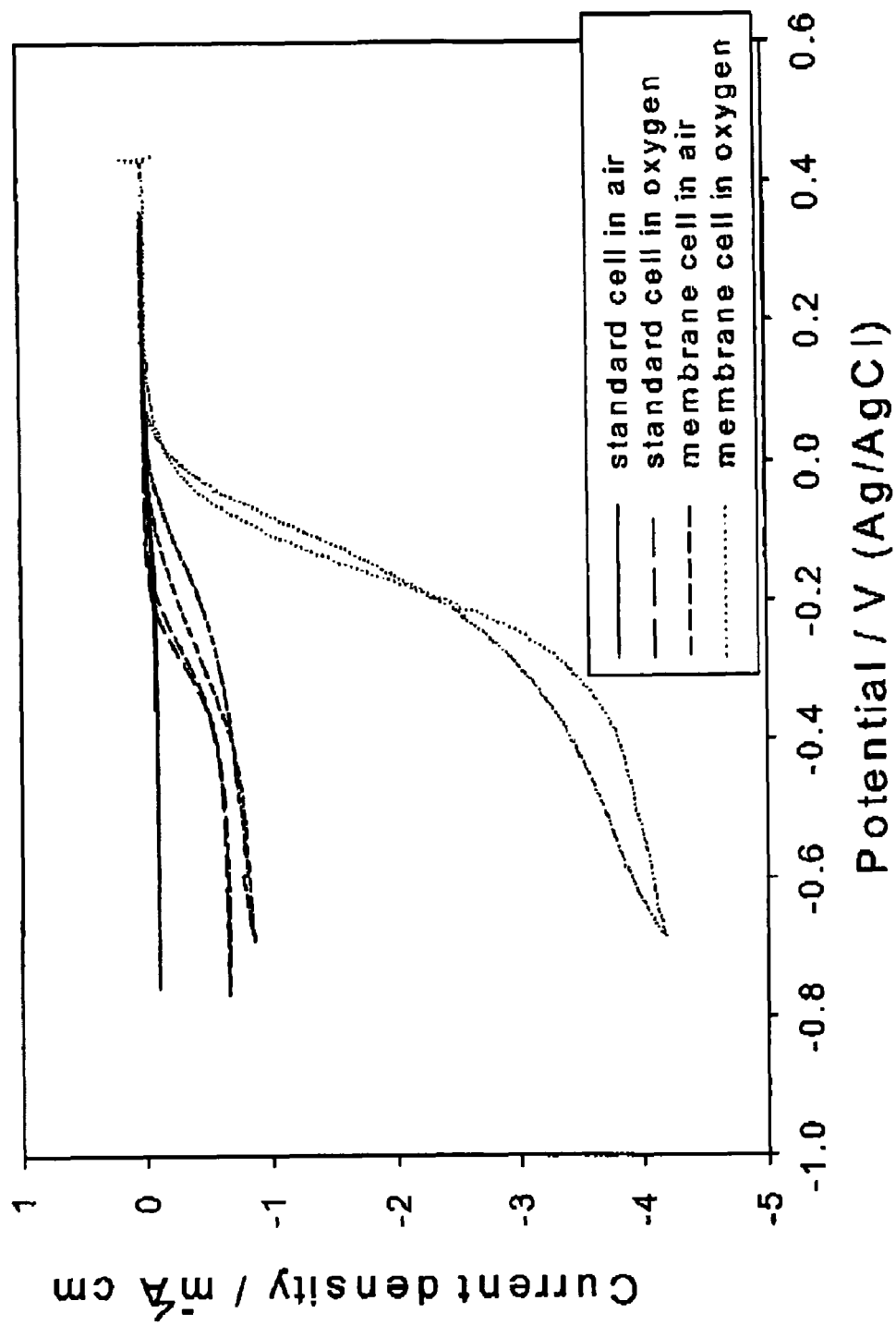
FIG. 4 is a graph of polarization curves for a microfluidic electrochemical cell and a standard electrochemical cell.
Figure 5:
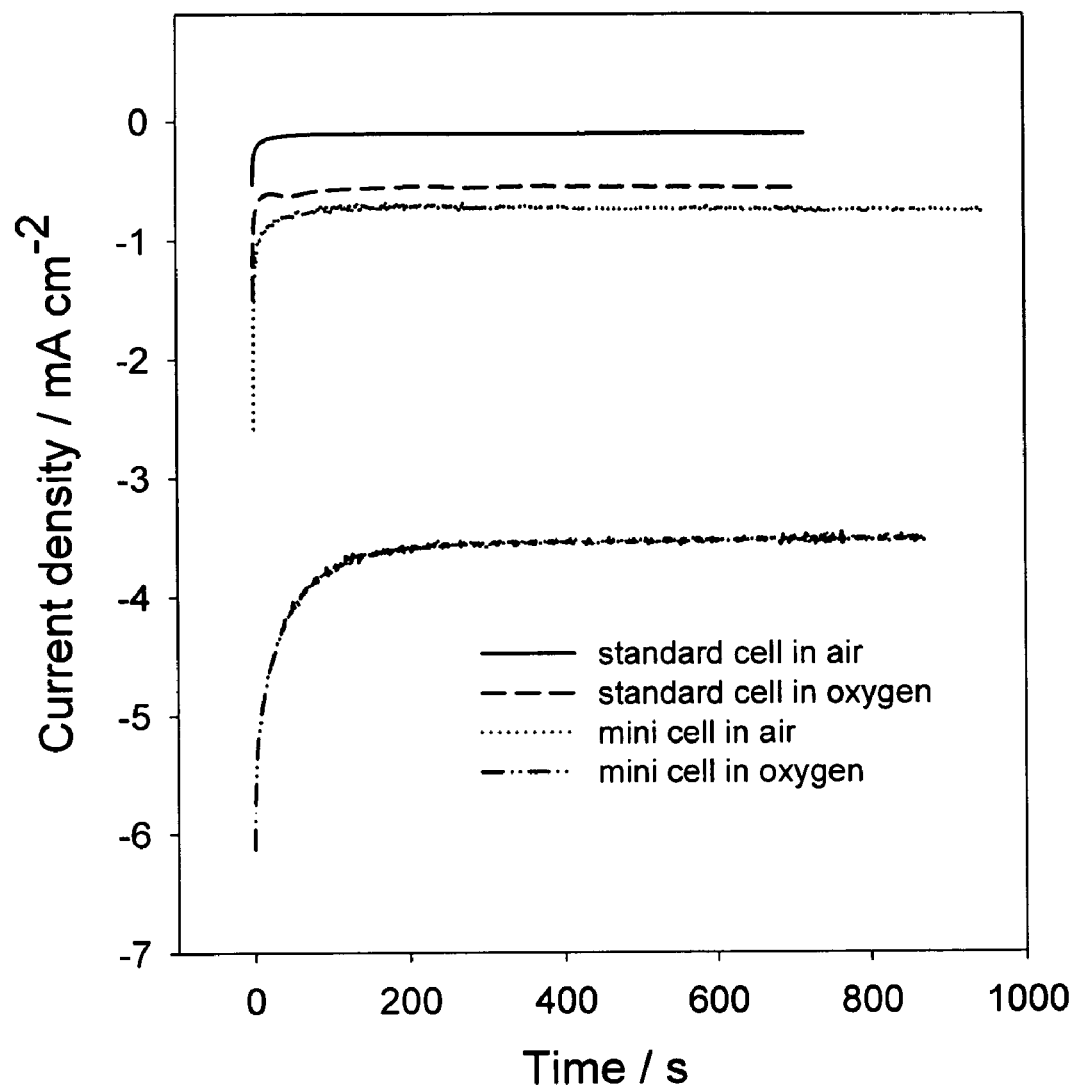
FIG. 5 is a graph of chronoamperometry curves for a microfluidic electrochemical cell and a standard electrochemical cell.

FIG. 4 illustrates polarization curves for a standard electrochemical cell, in which the bare electrode is submerged in a quiescent solution, and for a microfluidic electrochemical cell (designated "membrane cell"). These polarization curves plot the current density versus the electric potential applied to the electrode. The measured electric current was the result of the electrons consumed by the ORR, and a higher current density correlated with an increased rate of reaction in the ORR. FIG. 5 illustrates chronoamperometry curves for a standard cell and a microfluidic cell (designated "mini cell"). These chronoamperometry curves plot the current density versus time when an electric potential of −0.58 volts (V) was applied to the electrode (vs. Ag/AgCl). The data lines correlate with the legend from top to bottom. The experimental details related to these results are provided below in Example 3.

Both the polarization curves and the chronoamperometry curves show that the microfluidic cell provides much larger current densities than the standard cell. These results were seen both when the cells were in contact with air and when the cells were in contact with oxygen. The current densities in the microfluidic cell were at least three to five times greater than those observed in the standard cell. When the top membrane portion of the channels in the microfluidic cell is further reduced in thickness, the current density can be further improved, providing for an order of magnitude increase relative to a standard cell.

One possible explanation for the increase in reaction rate for the ORR is that it is related to one or more features of the microfluidic reactor. One feature of the microfluidic reactor is the solubility of oxygen in the gas permeable membrane, which is greater than the solubility in the electrolyte solution. For the cells used in the studies of FIGS. 4 and 5, the gas permeable polymer was PDMS, and the electrolyte was 0.1 molar (M) aqueous potassium chloride (KCl).

Yet another feature of the microfluidic reactor is the relatively small thickness of the gas permeable polymer membrane. It is believed that the small dimension of the membrane enables the gas depletion layer to extend through the membrane to the outer gas atmosphere. In this regime, the electrical current supported by the reactor is determined by the higher partial pressure of the reacting gas in the outer atmosphere, and not by its solubility in the polymer and/or the electrolyte.

Yet another feature of the microfluidic reactor is the relatively high electrode surface area in contact with the electrolyte solution. This large surface area can support large ORR currents and can deplete the electrolyte solution of the dissolved gas. Yet another feature of the microfluidic reactor is the occurrence of fluid flow within the microchannels. This fluid flow is believed to be due to pH gradients resulting from the generation of $OH^-$ ion by the ORR. The fluid flow is believed to facilitate the removal of reaction products from the electrode surface and the replenishing of reactants at the electrode surface.

The performance of the microfluidic reactor is related to a number of design parameters, including the thickness of the top membrane of the channels, the ratio of the exposed surface area of the electrode to the amount of dissolved gas in the channels as well as in the polymer membrane, and the permeation properties of the gas permeable membrane. The dimensions of the reactor and the materials used to make the reactor may be modified depending on the performance needs of the final application. For example, electrochemical reactors may be incorporated into a variety of devices, including gas sensors, fluid actuators and fuel cells, and a microfluidic electrochemical reactor can be configured for use in any or all of these devices.

The ratio of the exposed surface area of the electrode to the amount of dissolved gas in the channels can affect the reaction rate in a microfluidic reactor by influencing the amount of gaseous reactant in the electrolyte and within the membrane. The exposed surface area of the electrode is the portion of the electrode surface that is in contact with the channels, and thus with any electrolyte in the channels. This area can be increased by various roughening procedures such as electrochemical deposition or dealloying methods such that the geometric area of the electrode in contact with the electrolyte remains unchanged, which is more suitable for miniaturization purposes. If the electrode surface is not smooth, the exposed surface area can be measured by cyclic voltammetry, in which the measured charge corresponding to hydrogen adsorption or desorption can be compared to the hydrogen adsorption/desorption charge of an electrode having an atomically smooth surface. For example atomically smooth platinum exhibits a hydrogen adsorption/desorption charge of 210 micro-Coulombs per square centimeter. For other metal electrodes, the roughness of the surface can be estimated by using impedance spectroscopy.

The amount of dissolved gas in the channels is defined as the volume of the electrolyte in the channels multiplied by the solubility of gas in the electrolyte at a given gas partial pressure ($P_{O2}$) in the outer atmosphere. For a given reaction and reactor materials (i.e. electrolyte solution, electrode material and gas permeable membrane), the amount of dissolved gas can be modified by changing the volume of the channels. The amount of dissolved gas in the membrane is defined as the volume of the membrane covering the channels multiplied by the solubility of the gas in the membrane at a given $P_{O2}$.

If the ratio of the exposed surface area of the electrode to the amount of dissolved gas in the channels is too large, there will be insufficient gas within the electrolyte, the membrane and in the outer atmosphere to support the reaction, in which case the current will drop effectively to zero. If this ratio is too small, the supply of the gaseous reactant to the electrode will be limited by the amount of dissolved reactant within the electrolyte. The latter scenario is effectively what occurs in standard electrochemical cells, in which there is an excess of the electrolyte in contact with the electrode. Preferably, the ratio of the exposed surface area of the electrode (in square millimeters ($mm^2$) to the amount of dissolved gas in the channels (in moles) is from $3.0 \times 10^9$ to $3.0 \times 10^{12}$. More preferably, this ratio is from $1.5 \times 10^{10}$ to $3.0 \times 10^{11}$. Even more preferably, this ratio is from $3.0 \times 10^{10}$ to $1.5 \times 10^{11}$.

One possible explanation for the measured results is that, within the above ratios, the diffusion layer extends into the top gas permeable membrane. The diffusion layer is the portion of the electrolyte adjacent to the electrode surface in which there is a concentration gradient of the reactant of interest. At distances beyond the diffusion layer, the concentration of the reactant is constant. Within the diffusion layer, the reaction rate can be limited by the rate of diffusion of the reactant through the layer. Since gaseous reactants can have much higher solubilities and diffusion constants in gas permeable polymers than in electrolyte solutions, the reaction at the electrode can be increased if the diffusion layer extends into the gas permeable membrane. The supply of dissolved gaseous reactant in the electrolyte can be continually replenished by the gas present in a much higher concentration in the gas permeable membrane.

The thickness of the top membrane of gas permeable polymer can affect the reaction rate in a microfluidic reactor by influencing the rate at which the gaseous reactant is supplied to the channels. If the membrane is too thick, the reaction can be limited by the diffusion of the gas through the polymer. While this scenario may still provide for increased reaction rates relative to standard electrochemical cells, the reaction rate may be increased further by decreasing the thickness of the membrane. One possible explanation for this phenomenon is that the supply of dissolved gaseous reactant in the gas permeable membrane can be continually replenished by the gas that is present outside the microfluidic reactor. It is desirable that the membrane is as thin as possible while still maintaining its structural integrity. Preferably, the membrane thickness is from 1 micron to 2 millimeters. More preferably, the membrane thickness is from 5 microns to 1 millimeter. Even more preferably, the membrane thickness is from 10 microns to 500 microns.

Applications And Devices

Microfluidic reactors can be used for a wide variety of applications and devices. The increased electrochemical reaction rates provided by the microfluidic reactors can improve the performance of an electrochemical system that relies on a gaseous reactant. The configuration, dimensions and materials used for a microfluidic reactor will be dependent on the type of application desired.

Figure 6A:
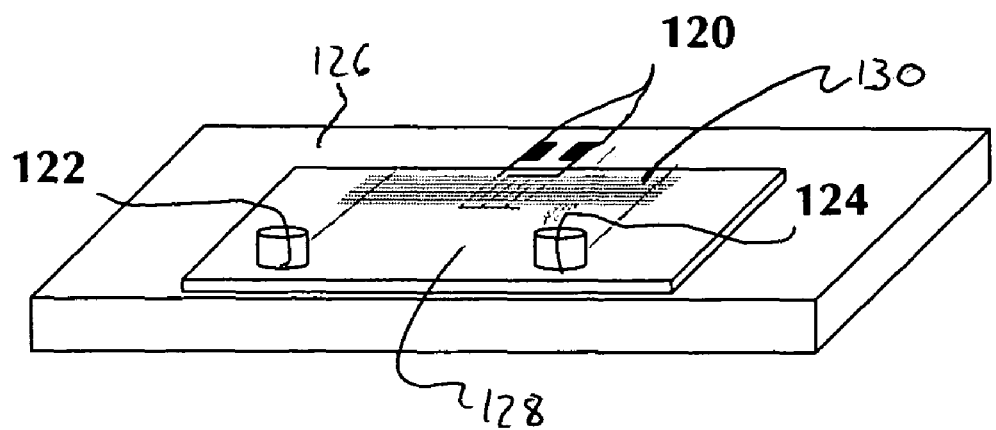
FIGS. 6A and 6B are schematic illustrations of a microfluidic electroanalytical cell, where 6A is a perspective view and 6B is a top view.
Figure 6B:
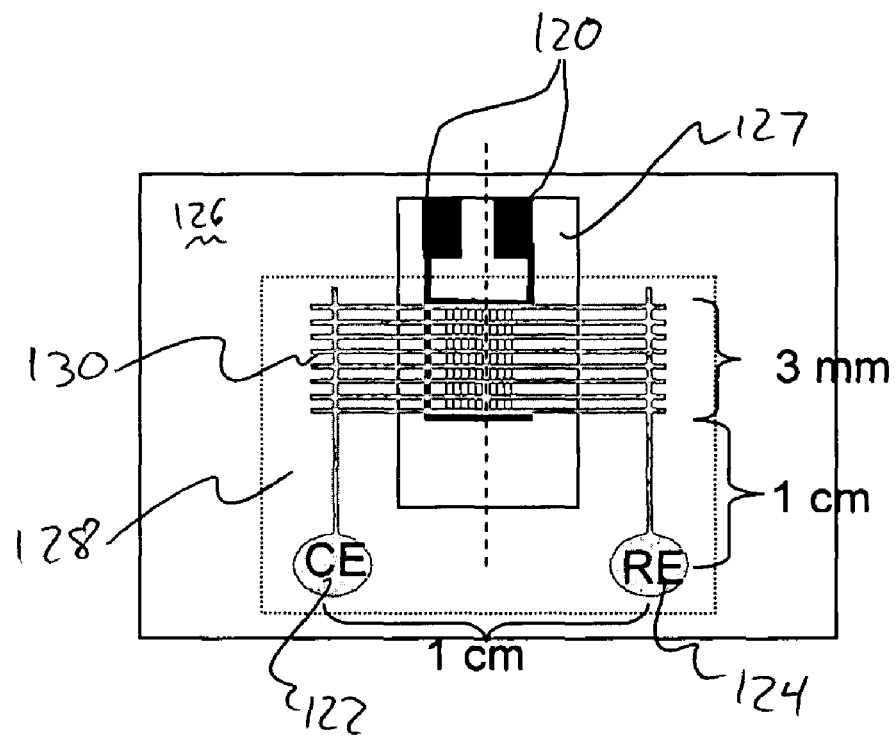

In one exemplary application, a microfluidic reactor can be configured as a component of an electroanalytical sensor. For example, a microfluidic reactor can be used as a working electrode. A counter electrode, and optionally a reference electrode, can be placed within the system such that they are in contact with the electrolyte that is present in the channels. Referring to FIGS. 6A and 6B, a microfluidic electroanalytical sensor may contain a working electrode 120, a counter electrode 122 and a reference electrode 124. The counter and reference electrodes are each in contact with the electrolyte that is present in the microfluidic channels 130. Although the counter and reference electrodes are illustrated at opposite ends of the network, other arrangements of the electrodes could also be used. The working electrode 120 is on a substrate 126, and the microfluidic channels 130 are present in a microfluidic network 128. The substrate 126 may be the secondary substrate, supporting optional primary substrate 127. The contacts from the working, counter and reference electrodes can be connected to a standard electroanalytical processor that allows the application of an electrical potential between the working and reference electrodes and that can measure the current between the working and counter electrodes.

In the example of the ORR, a microfluidic electroanalytical sensor can be used to measure the oxygen content of an environment. At a given applied potential, the current is related to the amount of oxygen present in the atmosphere surrounding the sensor. The electroanalytical sensor can be calibrated by measuring the current generated in atmospheres of known oxygen concentration. A microfluidic electroanalytical sensor can be much more sensitive than a standard electroanalytical cell, due to the larger currents generated by the ORR for the microfluidic system.

In another exemplary application, a microfluidic reactor can be configured as a component of a fuel cell. For example, one microfluidic reactor can be used as a cathode to support the reduction of oxygen, while a second microfluidic reactor can be used as an anode to support the oxidation of hydrogen, methanol or formic acid. Referring to FIG. 7, a microfluidic fuel cell may contain a cathode 150 and an anode 152 on a substrate 154. The electrodes are covered with a microfluidic channels 160 in a microfluidic network 156. Oxygen can then be introduced through inlet 157 to provide the gaseous oxidant in contact with an area of the gas permeable membrane over the cathode. The reductant can be introduced through inlet 158 to provide the reductant in contact with an area of the gas permeable membrane over the anode. The reductant can be a gaseous reactant such as hydrogen, or it can be a liquid reactant capable of permeating through the gas permeable membrane, such as methanol or formic acid.

The cathodic reaction in such a microfluidic fuel cell is the ORR at the cathode. The cathode may be a platinum electrode, or it may be a selective material that is active in the oxygen reduction reaction and inactive for oxidation of the oxidant. Examples of selective cathode materials include gold (Au), metal oxides, and platinum alloys such as Pt—Fe, Pt—Co or Pt—Ni. The anodic reaction may be carried out using the appropriate electrode material for the reductant. Typical anode materials include, for example, platinum, platinum treated with palladium, and platinum treated with ruthenium. When an electrical load is applied between the electrodes, an electric current is generated. For a given set of electrode materials and reactants, a fuel cell containing a microfluidic reactor at the cathode and/or anode can provide for increased current densities relative to those provided either by bare electrodes in solution or by electrodes completely covered with a gas permeable membrane. Increased current densities can result from the increased reaction rates at the electrodes in the microfluidic reactors, due to the rapid supply of gaseous reactant through the gas permeable membrane.

Fuel cells incorporating microfluidic electrochemical reactors at the anode and cathode can provide for improved power densities and current densities relative to other microfluidic fuel cells or to biofuel cells. In addition, fuel cells incorporating microfluidic electrochemical reactors may be completely passive systems. No pumps are needed to supply reagent to the anode or cathode, even when the fuel is a liquid such as formic acid or methanol.

In another exemplary application, a microfluidic reactor can be configured as a component of a fluid actuator, which is capable of pumping liquids in the microchannels. For example, a microfluidic reactor can be used for a reaction that produces a change in pH in the electrolyte in the channels, and the fluid can then spontaneously flow in the direction of the pH gradient. Referring again to FIG. 6, when an electrochemical reaction that consumes a gaseous reactant and produces either hydroxide ions or protons is carried out at the surface of the electrode 120, a pH gradient is established between the electrolyte near the electrode and the electrolyte away from the electrode near the counter electrode 122 and reference electrode 124. Microfluidic actuators incorporating microfluidic electrochemical reactors can provide for fluid flow at low applied voltage, such as from 0.1 to 1.0 volt.

Figure 8:
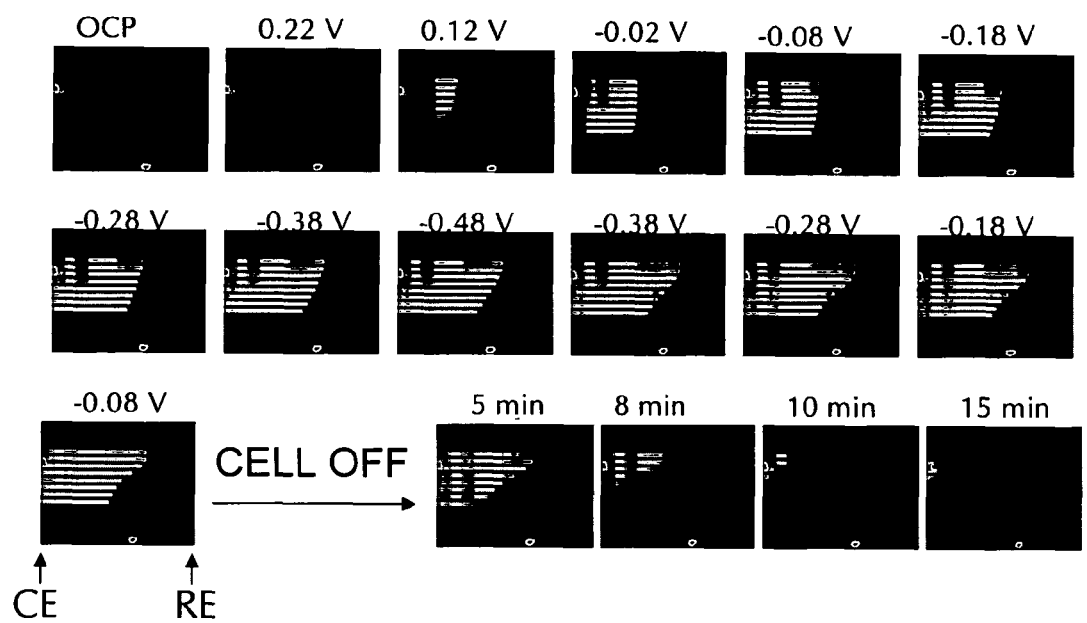
FIG. 8 is a set of images of fluorescence micrographs of a microfluidic electrochemical cell during operation.

In the example of the ORR, when the electrolyte is not buffered, the production of $OH^-$ by the reaction at the electrode influences the interfacial pH, such that the reaction can be imaged with a pH-sensitive dye. For example, fluorescein is converted to its fluorescent form by reaction with hydroxide and can thus be used as an indicator of the pH profile in the channels due to the progress of the ORR. FIG. 8 illustrates fluorescence micrographs of a 0.1 M KCl electrolyte (pH=4) containing 0.1 millimolar (mM) fluorescein as the electric potential was changed. These fluorescence micrographs were obtained throughout the reaction at every 100 millivolts (mV) during the potential scan. As the reaction progressed, the fluorescence appeared and then began to spread along the channels. The counter electrode is designated as CE, and the reference electrode is designated as RE. The pH gradient that was generated between the electrode and the rest of the network drove the motion of the hydroxide ions away from the microfluidic reactor, resulting in deprotonation of the fluorescein molecules along the channels and an increase in the fluorescence intensity. The flux of hydroxide ions generated at the electrode increased with time and became responsible for the flow of electrolyte from the area of the reactor towards the reservoirs. The fluorescence micrographs of FIG. 8 indicate that the fluid flowed in one direction during the scan and in another direction after the cell was switched off. The continuous fluid motion through the channels during the scan induced a pressure difference between the two reservoirs that was sufficient to cause an observable hydraulic fluid flow after the cell had been turned off.

One possible explanation for the increase in reaction rates provided by microfluidic reactors is that there is a contribution from convection within the channels. This convection is due to the fluid flow, which is driven by the pH gradient. This continuous fluid motion in the channels increases the convective transport of oxygen to the electrode and enables fresh, oxygen-saturated electrolyte to flow over the electrode. The magnitude of the pH gradient can be adjusted by changing the design or operating conditions of the fluid actuator. For example, increasing the current density at the working electrode can increase the pH gradient. In another example, the length of the gradient depends on the distance between the working electrode and counter electrode, such that a shorter distance will provide a larger gradient and a faster flow rate for a given set of conditions.

In another exemplary application, a microfluidic reactor can be configured as a component of system for performing chemical reactions and separations at the microfluidic level. The pH changes caused by performing the ORR at the electrode can be used to activate reagents that are sensitive to pH within a microfluidic system. For example, an array of microfluidic reactors may be used to cause a change in pH and to activate a pH-sensitive reagent, providing for localized chemical reactions at specific, addressable locations. Referring again to FIG. 8, the stable pH gradients generated by a microfluidic reactor may be used for separations of molecular species by isoelectric focusing. Microfluidic reactors are capable of sustaining a pH gradient even after the electrical circuit has been turned off. In addition, the typical problem of adsorption of the analytes at the electrodes may be avoided, as the pH gradient is generated at a distance from the electrode surface.

Fabrication of Microfluidic Electrochemical Reactors

A microfluidic electrochemical reactor can be made by covering an electrode on a substrate with one or more microfluidic channels having a top membrane containing a gas permeable polymer. The walls of the channels of the microfluidic network may also be made of a gas permeable polymer. It may be desirable for the microfluidic network to be irreversibly attached to the substrate. The term "irreversibly attached," as used herein, means that the bonding between two substances is sufficiently strong that the substances cannot be mechanically separated without damaging or destroying one or both of the substances. Substances that are irreversibly attached may be separated by exposure to an appropriate chemical environment, such as chemical reagents or irradiation.

An electrode material can be formed on a substrate by a variety of known methods. Metals may be deposited on a substrate, for example, by chemical vapor deposition or by deposition of a metal foil. Conductive carbon may be deposited, for example, by pyrolysis of a carbon-containing material. Slurry deposition may also be used for metals, conductive carbon, or mixtures of the two. An electrode for a microfluidic electrochemical reactor can also be a pre-formed electrode, such as a commercially available interdigitated electrode.

Figure 9:
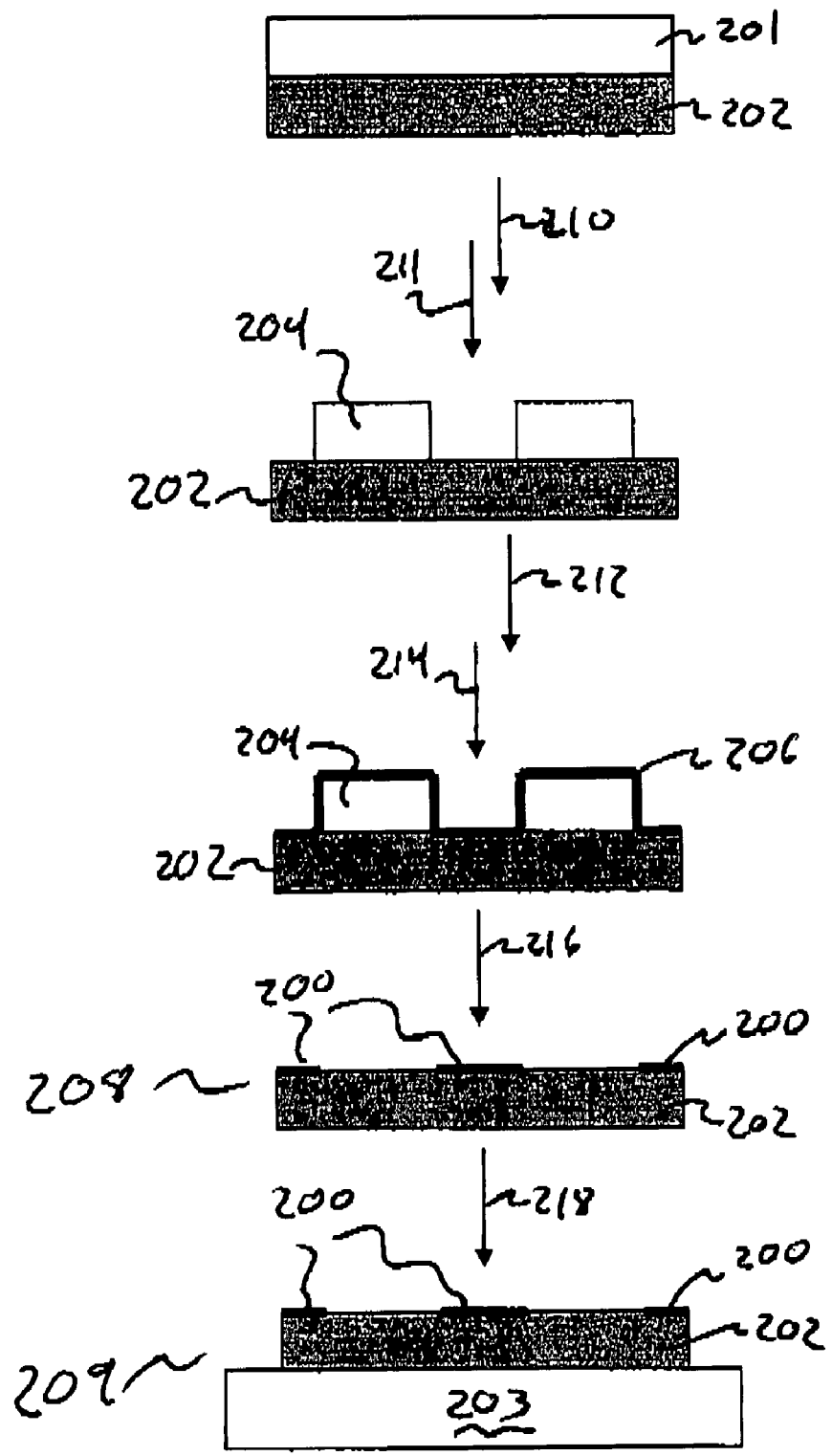
FIG. 9 is a diagram of a method of forming a patterned thin film electrode on a primary substrate.

Referring to FIG. 9, an electrode 200 may be formed on a substrate 202 using lithographic techniques and electron beam evaporation. In this method, a patterned photoresist 204 is formed on substrate 202 by exposing a layer 201 of the photoresist to appropriate radiation 210 through a patterned mask. Developing 211 the photoresist and substrate in an appropriate solvent provides the pattern in the photoresist by removing either the exposed or unexposed portions of the photoresist, depending on whether a positive or negative photoresist is used, respectively. The substrate 202 containing the patterned photoresist 204 can be cleaned and/or treated 212 with any desired surface treatment or adhesion layers. The metal for the electrode material is then deposited 214 as a layer 206 on the entire surface by electron beam evaporation. Removal 216 of the metal-coated photoresist leaves behind a patterned layer 200 of electrode material on the substrate. This electrode structure 208 can be covered with a microfluidic network and used in a device, or it can be further supported 218 by a secondary substrate 203 to provide structure 209. Provision of a secondary support may be desirable if the intended substrate for the microfluidic reactor or device is inappropriate for the deposition of the electrode material. The substrate 202 can be adhered to the secondary substrate 203, for example by the use of an adhesive layer between the substrate materials. The substrate 202 can also be mechanically attached to the secondary substrate 203, for example by the use of screws, rivets, clamps, or tongue-and-groove joints.

Figure 10:
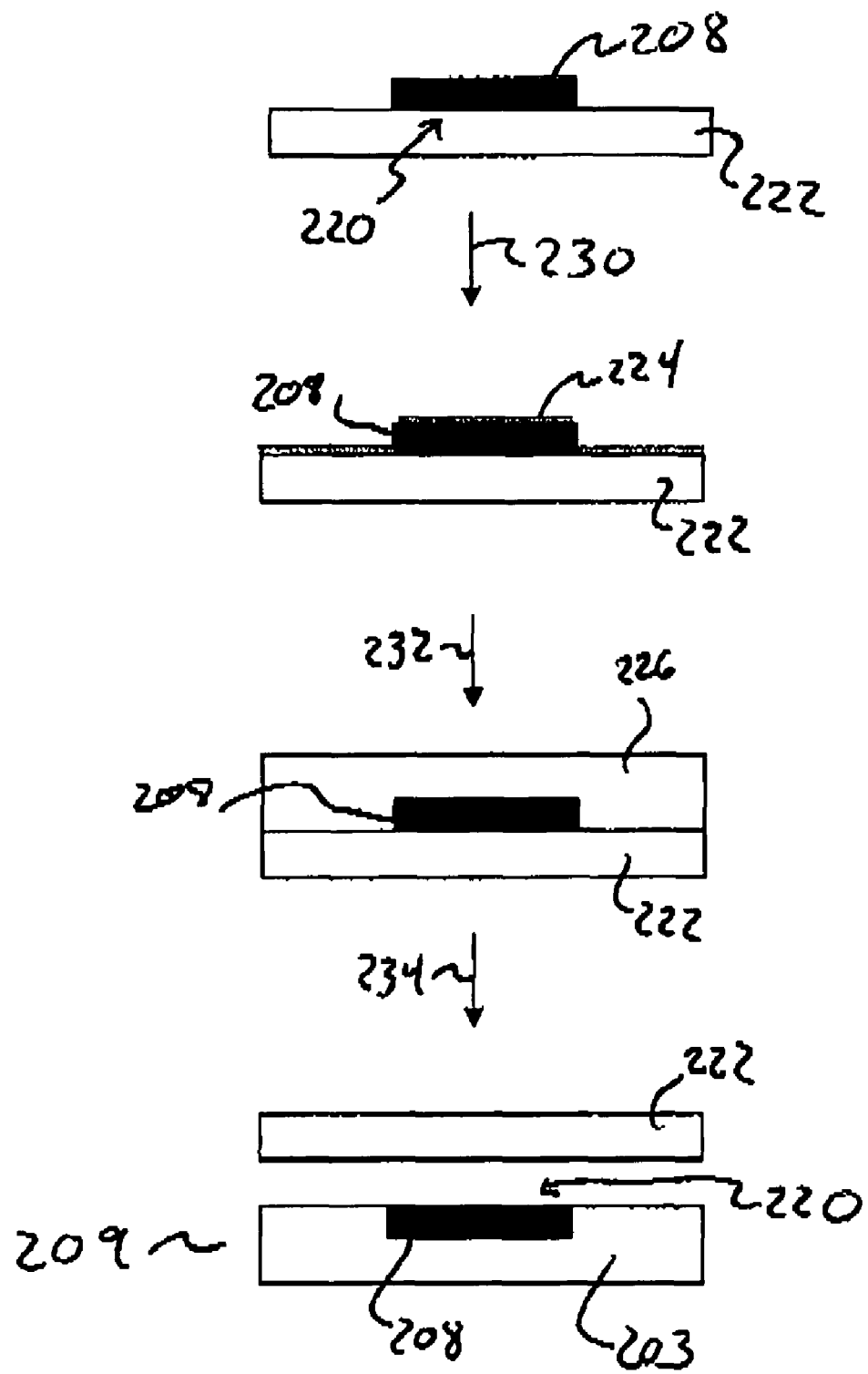
FIG. 10 is a diagram of a method of incorporating an electrode on a primary substrate into a secondary substrate.

Referring to FIG. 10, an electrode structure 208 is preferably embedded into a secondary substrate 203 so as to provide a planar surface on the electrode side 220 of structure 209. More preferably, this embedding process is carried out using silicon-containing elastomers. In this example, the electrode side 220 of structure 208 is placed in contact with a silicon-containing elastomer 222. The structure 208 and elastomer 222 are then treated 230 with an adhesion control agent 224. A layer 226 of prepolymer for a silicon-containing elastomer is then deposited 232 onto the treated surface and cured to form the secondary substrate 203. Removal 234 of the elastomer 222 thus exposes the patterned electrode. This embedding method can be used for custom fabricated electrodes as illustrated in FIG. 9, or for pre-formed electrodes.

A microfluidic network can be formed on the electrode by a variety of methods. For example, the side walls of the microfluidic channels can be formed by depositing a layer of material on the electrode structure and forming a pattern in the material through lithographic techniques. A membrane of gas permeable polymer can then be applied over the structure to form the tops of the channels. In another example, the microfluidic network can be fabricated separately by forming open, interconnected channel structures in a layer of gas permeable polymer. This patterned polymer can then be irreversibly attached or removably attached to the electrode structure, such that the electrode side of the structure forms the bottoms of the channels to complete the microfluidic network. It may be desirable to form the microfluidic network separately and then to attach the network to the electrode structure, so as to minimize the risk of damaging the electrode and substrate. The gas permeable membrane may be formed at the same time and from the same material as the microfluidic network, or the gas permeable membrane may be applied after the network is formed or after the network is attached to the electrode and the substrate.

The use of a silicon-containing elastomer as the polymer for the microfluidic network allows for either the irreversible attachment or the removable attachment of the network to the electrode structure. This attachment is described, for example, in U.S. Pat. No. 6,805,809 B2, which is incorporated herein by reference. In general, this method of attachment includes the oxidation of the surface of the gas permeable, silicon-containing elastomer, followed by the bonding of the oxidized surface to the surface of the other silicon-containing material.

Oxidation of silicon-containing elastomers can be performed by a variety of methods known in the art. In one method, for example, the elastomer can be exposed to an oxygenated plasma to oxidize the elastomer surface. This oxidation can be carried out by converting a stream of oxygen into a plasma at a temperature as low as 40° C. In another method, which is preferred, oxidation of a surface of a silicon-containing elastomer is performed by exposing the surface to ultraviolet radiation which is sufficient to generate ozone and/or other oxidizing species, such as singlet oxygen, from an ambient atmosphere. This particular oxidation is referred to as UV/Ozone treatment, or "UVO." Oxidation by UVO can also include exposing the surface to an atmosphere enriched in either molecular oxygen ($O_2$) or ozone ($O_3$). One advantage of the oxidation by UVO is that the silicon-containing elastomer can become sufficiently oxidized under mild conditions. See for example Ouyang, M. et al. *Chem. Mater.* 2000, 12, 1591-1596.

The oxidized surface of a silicon-containing elastomer can be irreversibly attached to the surface of a substrate material by contacting the oxidized surface and the substrate and bonding together the surface and the substrate. Suitable substrates include, but are not limited to, silicon; ceramic materials such as silicon oxide, quartz and glass; polymers such as polystyrene and silicon-containing elastomers, including PDMS; and metals such as titanium, chromium, tungsten, and gold. Preferably, the surface of the silicon-containing elastomer is treated with UVO at ambient temperature for an appropriate length of time and is then immediately contacted with a substrate that has been recently cleaned. For example, PDMS is preferably exposed to UVO for 1-4 minutes, more preferably for 2-3 minutes, and even more preferably for 2.5 minutes.

The elastomer and substrate are kept in contact to allow the formation of an irreversible bond. The contacted elastomer and substrate may be subjected to heating and/or supplemental ultraviolet radiation to assist the formation of the bond. For example, after contacting UVO treated PDMS with a silicon substrate, the irreversible bond can be obtained by maintaining the contact for about 16 hours at ambient temperature, by maintaining the materials at 70° C. for at least 20 minutes, or by applying UV radiation to the PDMS for at least 30 minutes. Exposure of unoxidized silicon-containing elastomers to only one of heat, ozone or UV radiation will not typically provide irreversible adhesion to substrates.

The initial contact between the oxidized surface of the silicon-containing elastomer and the substrate surface typically will not result in an irreversible bond. This phenomenon allows for the precise positioning of the elastomer and the substrate. Thus, any patterns in the elastomer and/or the substrate can be aligned or registered prior to the formation of an irreversible bond. The use of an optically transparent silicon-containing elastomer (such as PDMS) may also be desirable, in that alignment or registration of films and patterns can be done using optical observation.

It may be desirable to clean the surface of the substrate prior to contacting the substrate with the oxidized silicon-containing elastomer. Substrates may be cleaned by conventional methods. For example, substrates of silicon or silicon oxide can be rinsed with solvents such as hexanes and ethanol and dried under an inert gas such as nitrogen. In another example, glass and quartz can be rinsed with reagents such as piranha (sulfuric acid and hydrogen peroxide). The substrate may also be cleaned and/or oxidatively modified by exposure to UVO, to a plasma such as an argon plasma or other plasma, or to other chemical treatments. It may also be desirable to treat the surface of the substrate with UVO immediately prior to contacting it with the oxidized elastomer. The treatment of the substrate may conveniently be carried out by subjecting the elastomer surface and the substrate surface to the same UVO exposure. For metal substrates such as gold, it may be useful to apply an adhesion promoter such as a thiol compound to the metal surface and/or the elastomer surface. Examples of thiol compounds include thiol-silane compounds such as (thiolpropyl)-trimethoxysilane.

Ultraviolet radiation at 185 nm is believed to convert oxygen into ozone, which is subsequently converted to atomic oxygen by UV radiation at 254 nm. It is believed that oxidation of the silicon-containing surface of the elastomer serves to form free silicon-oxide (Si—O—) and/or silicon-hydroxide (Si—OH) functionalities on the surface due to the removal of organic groups by cleavage of the initial silicon-oxygen-carbon (Si—O—C—) or silicon-carbon (Si—C) bonds. Contact between the oxidized elastomer and the substrate is believed to foster the formation of silyl ether (Si—O—Si, Si—O—C, or Si—O-metal) bonds between the two materials.

The amount of UVO treatment may be varied depending on the type of silicon-containing elastomer and the type of substrate material. For example, for polysiloxanes containing alkyl or aryl organic side groups which are less volatile than the methyl groups of PDMS, the UVO may need to be applied for more than 5 minutes. Also, for silicon-modified elastomers and polysiloxane-containing block copolymers, an increased duration of UVO may be needed, since the silicon atoms are less concentrated than in PDMS. PDMS elastomer which has been treated with UVO for 5 minutes or more may not adhere to a substrate irreversibly, and treatment for 4 minutes may yield adhesion which is inconsistent from one sample to another. Other silicon-containing elastomers may also exhibit this "overoxidation" phenomenon and thus will have a maximum effective UVO treatment time.

In addition to being irreversibly attached to a substrate, the oxidized surface of a silicon-containing elastomer can be adhered to a transfer pad material such that the attachment is removable. The term "removably attached," as used herein, means that the bonding between two substances is sufficiently weak that the substances can be separated mechanically without significantly damaging either substance. A silicon-containing elastomer can be adhered to a transfer pad with a bond which is sufficiently strong to allow for manipulation of the elastomer, but which is less strong than the cohesive forces within the elastomer. Thus, the removable attachment between a silicon-containing elastomer and a transfer pad can allow the elastomer to retain its desired shape during storage and/or other processing, but the elastomer can be completely removed from the transfer pad when they are pulled away from each other with a sufficient force. Preferably, this removal is accomplished without tearing the elastomer and/or the transfer pad (cohesive failure).

The removable attachment of a silicon-containing elastomer to a transfer pad may be facilitated by the combination of oxidation of the surface of the elastomer and deposition of an adhesion control agent on the oxidized surface. For example, the surface of a silicon-containing elastomer can be oxidized and then exposed to an adhesion control agent such that at least some of the adhesion control agent is present on the surface. Contacting this modified surface with a transfer pad can then provide the elastomer and the transfer pad connected by a removable attachment.

Adhesion control agents can be any substance which, when present on an oxidized surface of a silicon-containing elastomer, reduces the strength of the bond between the oxidized surface and another material. Adhesion control agents may include, but are not limited to, surface active agents such as ionic and non-ionic surfactants, silane compounds such as a trichlorosilane containing an organic substituent, siloxane compounds such as a cyclic methylsiloxane containing an organic substituent. Preferred adhesion control agents include trichlorosilanes containing an organic substituent having from 3 to 20 carbon atoms. More preferred adhesion control agents include trichlorosilanes containing a fluorinated organic substituent having from 3 to 20 carbon atoms and from 1 to 41 fluorine atoms. A specific preferred adhesion control agent is (tridecafluoro-1,1,2,2-tetrahydrooctyl) trichlorosilane (TDTS).

Removable attachment may also be facilitated by a stimulus-responsive adhesive layer between the elastomer and the transfer pad. The adhesive layer can provide an irreversible attachment between the adhesive layer and the silicon-containing elastomer and between the adhesive layer and the other material, but can be made to reduce the strength of attachment to the elastomer and/or the other material. For example, a layer of adhesive material may be subjected to a change in conditions such as temperature, irradiation or electric field such that the adhesive strength is reduced. In one example, a photoresist material such as poly(methyl methacrylate), poly($\alpha$-methylstyrene), poly(norbornene-co-maleic anhydride), or phenol-formaldehyde can initially provide an adhesive bond between the materials. These materials may then be degraded by irradiation to sufficiently reduce the strength of adhesion and to allow the materials to be separated. Such photoresist-based reversible adhesion may also include the use of a photosensitizer such as a photoacid generator to improve the response time for the reduction in adhesive strength.

Suitable transfer pad materials include, but are not limited to, silicon, silicon oxide, quartz and glass, as well as silicon-containing elastomers such as PDMS. Preferably, the transfer pad is a silicon-containing elastomer. More preferably, the transfer pad is PDMS.

Figure 11:
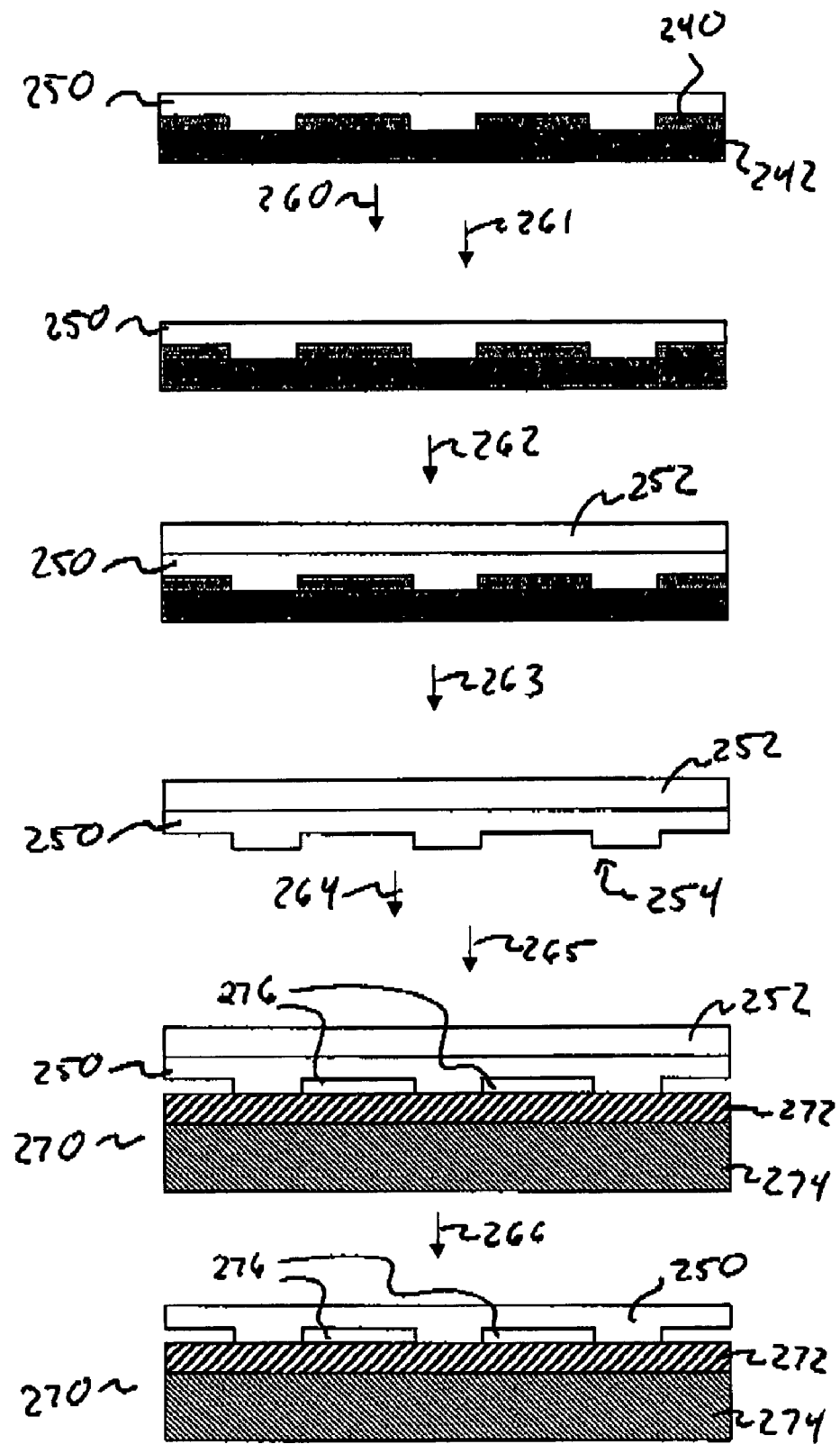
FIG. 11 is a diagram of a method of forming a microfluidic network and of forming a microfluidic electrochemical reactor including the network.

An example of the formation of a microfluidic network using the irreversible attachment of a silicon-containing elastomer is illustrated in FIG. 11. In this example, the silicon-containing elastomer is patterned as a microfluidic network based on a master pattern 240. The master pattern may be present on a surface of a master material 242. The master can be patterned by any number of known microfabrication techniques and can be made of a variety of materials. Preferably, the master is cleaned before deposition of material that is used to make the patterned elastomer. It is also preferred that the master not contain substances which can be transferred to the surface of the patterned elastomer, such as contaminants, lubricants, salts, particulates, small molecules, or oligomers.

Formation of the final silicon-containing elastomer 250 on the patterned surface of the master forms a relief of the pattern in the elastomer. Silicon-containing elastomers can be formed, for example, by polymerizing monomers and/or prepolymers; by crosslinking monomers, prepolymers and/or polymers; and by solidifying the elastomer from a liquid or molten state. Thus viscous elastomer precursors, such as monomers, prepolymers or uncrosslinked polymer, can be deposited onto the patterned surface of a master. Polymerization and/or crosslinking can then provide the patterned silicon-containing elastomer, which can be removed from the master. Also, an elastomer that is at a temperature above its melting temperature ($T_m$) can be deposited onto the patterned surface of the master. Once the elastomer has cooled sufficiently below its $T_m$, it can be removed from the master to reveal the patterned elastomer. When transferring a pattern using irreversible attachment and cohesive failure, it is preferred that the material used to make the patterned silicon-containing elastomer is deposited on the master in an amount sufficient to cover the entire master pattern.

Referring still to FIG. 11, the material used to make the microfluidic network is deposited on the master in an amount sufficient to cover the entire master pattern, such that a continuous film of the elastomer 250 covers the entire master pattern 240. Once the exposed continuous film surface is oxidized 260 and treated with an adhesion control agent 261, a transfer pad material 252 may be applied 262, in the form of a pre-solidified material or as an elastomer precursor that then solidifies. Once the film 250 is removably attached to the transfer pad 252, the film and transfer pad can be separated 263 from the master to expose the other surface 254 of the film 250. This exposed surface, which has been patterned based on the master pattern, can then be oxidized 264 and bonded 265 to a substrate, as described. In this example, the substrate is the electrode structure 270, containing an electrode 272 and a substrate for the electrode 274.

The electrode structure and the silicon-containing elastomer are thus irreversibly bonded along the pattern as dictated by the master pattern. When the transfer pad 252 is pulled away 266 from the electrode structure, the removable attachment will be broken, leaving a film 250 of elastomer material bonded to the electrode structure only in regions where the elastomer surface has been oxidized and then placed in contact with the electrode structure. If the removable attachment is provided by a stimulus-responsive adhesive between the elastomer and the transfer pad, the oxidation 260 and adhesion control treatment 261 may be substituted with a deposition of the stimulus-responsive adhesive. Also, once the pattern has been oxidized 264 and irreversibly bonded 265, the adhesive is subjected to appropriate conditions to sufficiently reduce the strength of attachment between the transfer pad 252 and the film 250 before removing 266 the transfer pad from the electrode structure. The interconnected spaces 276 formed between the film and the electrode structure are the channels of the microfluidic network.

The transfer pad may be a solid material before it is contacted with the elastomer film, or the transfer pad may be formed directly on the elastomer film after the surface has been oxidized and treated with adhesion control agent. The formation of the transfer pad on the oxidized and treated surface is especially useful when the transfer pad is a silicon-containing elastomer. Thus, a viscous elastomer precursor can be deposited on the oxidized and treated film surface and allowed to solidify into an elastomeric transfer pad. The elastomeric transfer pad will then be removably attached to the film upon formation of the transfer pad.

In an example of the formation of an elastomeric transfer pad on an oxidized and treated film, initiated PDMS precursors can be deposited on a film surface and allowed to polymerize into a PDMS elastomer. Typically, when initiated PDMS precursors are added to a portion of PDMS which has already been cured, for example an elastomer film, the newly formed layer cures without the formation of a measurable boundary between the layers. Thus, the "adhesion" between the layers is the bulk, internal adhesion, which is relatively strong. If the surface of the cured PDMS film has been treated with an adhesion control agent without oxidation, the adhesion between the film and the transfer pad layer will be less than the bulk adhesion, allowing the layer and the film to be separated without causing damage to either layer. The adhesion can be reduced further by exposing the cured PDMS film to UVO before depositing an adhesion control agent.

For a cured PDMS film that is subjected to UVO, the strength of adhesion can thus be controlled by adjusting the amount of adhesion control agent, with increased amounts of adhesion control agent correlating to decreased adhesion strength. For example, a cured PDMS film that is subjected to 50 seconds of UVO followed by 20 minutes of exposure to TDTS exhibits minimal adhesion to a PDMS transfer pad. A reduction in the TDTS exposure provides for removable attachment to the PDMS transfer pad, and the film is thus supported across the entire film-transfer pad interface, allowing the exposed surface of the film to be brought into contact with a substrate without tearing, sagging, or folding of the film. The strength of adhesion can also be controlled by changing the level of exposure to UVO before the addition of an adhesion control agent. If the type and amount of adhesion control agent is unchanged, an increase in the UVO treatment time can provide for a reduction in the adhesion strength.

The following examples are provided to illustrate one or more preferred embodiments of the invention. Numerous variations can be made to the following examples that lie within the scope of the invention.

EXAMPLES

Example 1

Electrochemical Cell Having Fabricated Platinum Electrode

A platinum (Pt) electrode was fabricated on a quartz slide using lithographic techniques (see, for example, FIG. 9). A positive photoresist (AZ 5214; CLARIANT, Sommerville, N.J.) was applied by spin casting to a quartz slide having dimensions of 4 mm×25 mm. After spin casting at 3000 revolutions per minute (rpm) for 30 seconds, the photoresist layer was cured at 100° C. for 1 minute. The photoresist was exposed to ultraviolet radiation (UV) through a photomask, using a contact mask aligner, for 6 seconds at 335 watts (W). The exposed regions of the resist were then removed, followed by rinsing with deionized water, to provide a structure having a photoresist pattern on the quartz slide. Titanium was deposited by electron beam evaporation onto the structure to provide an adhesion layer having a thickness of 0.015 μm. Platinum was then deposited by electron beam evaporation to provide a layer having a thickness of 0.1 μm. The electron beam evaporation was performed using an FC-1800 Electron Beam Deposition System (AIRCO-TEMESCAL). The metalized photoresist pattern was removed by treatment with acetone to provide the patterned platinum electrode on the quartz slide.

This structure was embedded into a secondary substrate (see, for example, FIG. 10). The quartz slide was placed onto a flat layer of poly(dimethylsiloxane) (PDMS) such that the Pt layer was between the quartz and the PDMS. The thickness of the PDMS layer was approximately 1 mm, while the width and the length of the PDMS layer were at least of the dimensions of the microfluidic network (2 cm×2 cm). The PDMS and quartz were then exposed to tridecafluoro-1,1,2,2-tetrahydrooctyl trichlorosilane at room temperature for 30 minutes to silanize the top surface. To the silanized surface was added a PDMS prepolymer, which was then cured at 70° C. for 2 hours, leaving the electrode sealed between the two PDMS layers. A 3 cm×3 cm portion of the entire sandwich structure was cut with a razor blade and pressed on a microscope glass slide such that the Pt layer was above the quartz. The top PDMS layer, which was the material from the original PDMS layer, was carefully peeled from the rest of the structure to expose the Pt layer. An electrical contact was formed by sealing a Pt wire to the contact pad portion of the electrode with a silver epoxy resin (EPO-TEK 4110, EPOXY TECHNOLOGY, Billerica, Mass.).

This electrode structure was then incorporated into a microfluidic electrochemical cell (see, for example, FIG. 11). First, a master structure was produced by preparing a pattern of photoresist on a silicon substrate. Contact photolithography was used to make master patterns by patterning either SU-8 5 or SU-8 50 (MICROCHEM, Newton, Mass.) photoresists, using 5080 dpi transparencies as an exposure mask. Once the master structure was produced, a PDMS prepolymer was poured on the pattern. The amount of PDMS prepolymer deposited was sufficient to completely cover the pattern on the master structure. The prepolymer was cured at 70° C. for 2 h. Removal of the cured PDMS layer and irreversible bonding to the electrode embedded in PDMS provided the microfluidic electrochemical cell.

Thus, the dimensions of the photoresist pattern correlated to the dimensions of the channels in the microfluidic network, and the thickness of the first PDMS layer on top of the photoresist correlated to the thickness of the PDMS membrane defining the tops of the channels (see, for example, FIG. 6). The channels were 214 μm wide, 58 μm high, and were separated from each other by a distance of 180 μm. Each channel was 1 cm long, and the channels were connected at each end with a perpendicular channel having a length of 1.5 cm. These connector channels terminated in extension reservoirs. The channels were filled with electrolyte through the holes punched by a leather punch, using the capillary outgas technique. The capillaries were filled with the electrolyte by applying vacuum for 20 min. When the vacuum was released, the capillaries filled either spontaneously or with mild agitation. Extension reservoirs for the platinum counter electrode and the silver reference electrode were placed on top of the holes and the entire setup was placed in a poly(methyl methacrylate) box (PLEXIGLAS; ATOFINA CHEMICALS, Inc, Philadelphia, Pa.).

Example 2

Electrochemical Cell Having Platinum Interdigitated Electrode

A microfluidic electrochemical cell was constructed as described in Example 1, but using a commercially available Pt interdigitated electrode (Pt IDA). The Pt IDA was IME-1525.3 M-Pt-U (ABTECH SCIENTIFIC, Inc., Richmond, Va.), a monolithic, unpackaged electrode with 25 digit pairs having a digit length of 2.99 mm, a digit width of 15 μm, and an interdigit spacing of 15 μm. The Pt IDA was pressed into a flat layer of PDMS, and the structure was then exposed to tridecafluoro-1,1,2,2-tetrahydrooctyl trichlorosilane at room temperature for 30 minutes (see, for example, FIG. 10). To the silanized surface was added a PDMS prepolymer, which was then cured at 70° C. for 2 hours, leaving the electrode sealed between the two PDMS layers. A 3 cm×3 cm portion of the entire sandwich structure was cut with a razor blade and pressed on a microscope glass slide such that the Pt IDA was above the quartz. The top PDMS layer, which was the material from the original PDMS layer, was carefully peeled from the rest of the structure to expose the Pt IDA. An electrical contact was formed by sealing a Pt wire to the contact pad portion of the electrode with silver epoxy resin.

This electrode structure was then incorporated into a microfluidic electrochemical cell as described in Example 1. Two different microfluidic networks were employed. Network A was identical to that described in Example 1 (214 μm channel width, 58 μm channel height, 180 μm channel separation, 1 cm channel length, with 1.5 cm long perpendicular connector channels). Network B had similar dimensions, in which the channels of the microfluidic network were 200 μm wide, 50 μm high, and were separated from each other by a distance of 200 μm. Each channel in network B was 1 cm long, and the channels were connected at each end with a perpendicular channel having a length of 1.3 cm. A biopsy punch was used to form the holes for filling the microfluidic network with electrolyte using the capillary outgas technique. Extension reservoirs for the platinum counter electrode and the silver reference electrode were placed on top of the holes. The entire setup was placed in a PLEXIGLAS box.

Example 3

Voltammetry Using Microfluidic Electrochemical Cell

The electrochemical behavior of the microfluidic electrochemical cells of Example 2 with respect to the ORR was studied by linear sweep voltammetry. The electrochemical measurements included recording the cathodic polarization curves in argon, air and oxygen. The performance of the microfluidic electrochemical cells were compared to a standard electrochemical cell having a bare Pt IDA electrode in a three-compartment cell in quiescent solution. The reference electrode compartment in the cell was connected to the main body of the cell via a Luggin capillary, while the counter electrode compartment was separated from the main body by a porous glass frit. The electrochemical measurements of Examples 3-5 were performed (unless otherwise noted) in an unbuffered solution of 0.1 M KCl at pH=4. The pH of the solutions was adjusted by adding several drops of 0.1 M HCl. All chemicals used were of analytical grade, while the pure gases used (Smith Welding Supply, Champaign, Ill.) were of >99.99% purity.

A microfluidic cell as prepared in Example 2 was configured as an electroanalytical cell by inserting a platinum electrode in the reservoir for the counter electrode and inserting a silver electrode in the reservoir for the pseudo-reference electrode. No special pretreatment of the electrode was performed prior to the measurements. The leads from the working, counter and reference electrodes were attached to a PINE RDE 4 bipotentiostat (BIOANALYTICAL SYSTEMS, West Lafayette, Ind.). For the measurements performed with the microfluidic cell, the PLEXIGLAS box containing the cell was purged with the gas of interest at a flow rate of 42 mL/min for 1 hour. For the measurements performed with the standard cell, the electrode was immersed in the electrolyte, and the electrolyte was purged with the gas of interest for 1 hour prior to the measurements. During the measurements the gas was applied above the solution to avoid the formation of gas bubbles that could interfere with the measurement. The data from each type of electrochemical cell was acquired by a National Instruments data acquisition card using LabView software.

The oxygen reduction polarization curves were recorded from open-circuit potential (OCP) to the onset of hydrogen evolution at around −0.68 V and back to OCP at a scan rate of 1 mV/s. The shift in potential of the Ag wire pseudo-reference with respect to the Ag/AgCl reference electrode was calculated from the potential difference in the location of the $K_4(FeCN_6)$ oxidation peaks for the two reference electrodes at 5 mV/s and amounted to +120 mV. All potentials are referred to Ag/AgCl (3 M KCl).

Figure 12:
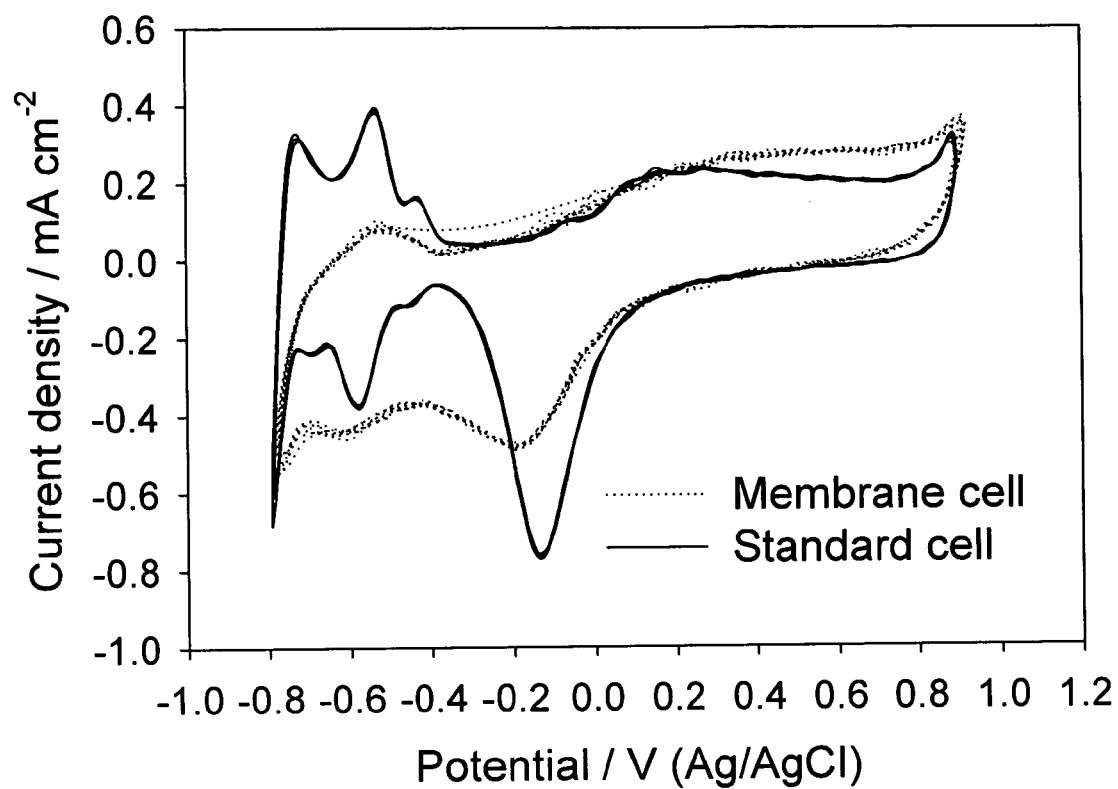
FIG. 12 is a graph of cyclic voltammetry curves for a microfluidic electrochemical cell and a standard electrochemical cell.

FIG. 12 shows the steady state cyclic voltammograms recorded in 0.1 M KCl in a 0.1 M Na-borate buffer at pH=10, for a bare Pt interdigitated electrode (IDA) immersed in a standard electrochemical cell and the same electrode in microfluidic network A, having a 2.1 mm thick PDMS membrane. The data for the standard cell corresponds to the solid line, and the data for the microfluidic cell corresponds to the dashed line. Both configurations showed the same characteristic platinum features of the oxide formation plateau, the oxide reduction and hydrogen adsorption-desorption peaks. The sharpness of the hydrogen adsorption-desorption peaks was notably smaller in the miniaturized cell and was caused by the significantly higher Ohmic resistance in the microchannels (around 0.5 MΩ) compared to that in the standard cell (several Ωs). The higher Ohmic drop in the microchannels was also responsible for the additional overvoltage in the Pt-oxide reduction region.

The cyclic voltammogram corresponding to the microfluidic cell revealed higher current densities in the hydrogen adsorption region and smaller current densities in the hydrogen desorption region compared to those measured in the conventional cell, which was caused by the cathodic oxygen reduction currents superimposed on the argon background. Those ORR currents originated from the traces of oxygen present in the membrane cell even after 1 h of argon purging. The purging with argon of the conventional cell appeared to be more efficient, with no ORR currents measured. The cyclic voltammograms of the electrode in the microfluidic cell were found to be stable during 200 cycles, indicating the electrochemical stability of the surface of the electrode under those electrochemical conditions.

FIG. 4 shows the polarization curves for ORR recorded in air and oxygen for the standard cell and the microfluidic cell (designated "membrane cell"). In the entire potential range, the ORR was significantly faster in the microfluidic cell, both in air and in oxygen. It should be noted that after the potential was applied to the electrode, fluorescence microscopy revealed some activity in the areas of the electrode that were not in direct contact with the electrolyte but were covered by the PDMS channel separations. The latter may be attributed to electrowetting probably taking place in the interfacial area between the electrode and the PDMS. However, even after taking into account the electrowetted electrode area for the current density calculation, the current densities in the microfluidic cell still exceeded those observed in the conventional cell by 3-5 times.

Example 4

Chronoamperometry Using Microfluidic Electrochemical Cell

The electrochemical behavior of the microfluidic electrochemical cells of Example 2 with respect to the ORR was also studied by chronoamperometry. The performance of the microfluidic electrochemical cells were compared to a standard electrochemical cell having a bare Pt IDA electrode in a three-compartment cell in quiescent solution as described in Example 3. The microfluidic cell was prepared, and the electrochemical data was collected and acquired as described in Example 3.

The electrochemical performance of the microfluidic cell and the standard cell were tested in different gas atmospheres (argon, air and oxygen) in 0.1 M KCl (pH=4) by stepping the potential from the open circuit (OCP) to −0.7 V vs. Ag and monitoring the ORR current over time. The transient behavior of the electrode was monitored for 15-20 min. The electrolyte in the conventional cell was fully saturated prior to the measurement by purging it with the gas of interest for 1 h, after which the gas was continuously supplied by a flow sustained above the solution during the measurement. For the microfluidic cell, the gas was flowed through the sealed PLEXIGLAS box for 1 h before and then continuously thereafter during the measurement. The current densities were calculated with respect to the geometric surface area of the electrode in contact with electrolyte. For the standard cell having a Pt IDA immersed in bulk electrolyte, this surface area was 0.0225 cm$^2$. The surface area was 0.0128 cm$^2$ for a microfluidic cell using network A, and 0.0123 cm$^2$ for a microfluidic cell using network B. The shift in potential of the Ag wire pseudo-reference with respect to the Ag/AgCl reference electrode was calculated from the potential difference in the location of the K$_4$(FeCN$_6$) oxidation peaks for the two reference electrodes at 5 mV/s and amounted to +120 mV. All potentials are referred to Ag/AgCl (3 M KCl). The chronoamperometric plots for the two electrochemical cells obtained in air and oxygen under these conditions are shown in FIG. 5.

The data in FIG. 5 reveal several features of the microfluidic cell relative to the standard cell. First, the diffusion-limited ORR currents measured in the microfluidic cell were remarkably stable during its operation. Second, diffusion-limited current densities obtained in the PDMS membrane covered microfluidic cell are significantly higher both in air and in an oxygen atmosphere, by approximately an order of magnitude. This current enhancement is even more pronounced when a thinner PDMS membrane is used. The superior performance of the microfluidic cell is believed to be due to the higher solubility of oxygen in PDMS than in the electrolyte as well as to an increased convective mass transport of oxygen in the microfluidic cell. The improved gas transport to the electrode is aided by the continuous fluid flow through the channels, which is spontaneously driven by the pH gradients generated by the oxygen reduction reaction in the microfluidic channels.

This data agrees well with the fact that the solubility of oxygen in PDMS ($1.72 \times 10^{-6}$ mol/cm$^3$) is around 6-7 times higher than that in 0.1 M KCl ($2.6 \times 10^{-7}$ mol/cm$^3$), while the diffusion coefficient of oxygen in PDMS ($3.4 \times 10^{-5}$ cm$^2$/s) is comparable to the one in 0.1 M KCl. The response time of the electrode in the microfluidic cell was somewhat longer, reflecting diffusion through two diffusion layers—one in the electrolyte and the other in the membrane.

The diffusion limiting current densities were found to increase with decreasing the membrane thickness for membranes thinner than 1.7 mm. Below a limiting value (<1 mm), thinner membranes yielded higher diffusion limited ORR current densities. Under these conditions, the superior performance of the microreactor is believed to be due to the fact that the gas depletion layer extends through the membrane to the outer atmosphere where the partial pressure of oxygen is higher than the oxygen solubility in the membrane as well as in the electrolyte. In cases when a reactant gas is continuously supplied to the membrane (for instance, in fuel cells) this is a preferred regime of operation of the reactor.

In order for the diffusion layer to spread from the surface of the electrode to the outer atmosphere (which is a preferred regime of operation) the amount of gas reacted at the electrode should equal the sum of the amount of the gas dissolved in the electrolyte and the one in the membrane. In this scenario, the current density is related to the parameters of the system by the following equation:

$$[R_f A j(t) dt]/(nF) = [(w_c l_c h_c n_c \alpha_{g,c}) + (w_m l_m z_m \alpha_{g,m})] P_g$$

$R_f$ is the roughness factor of the electrode, defined as the ratio of the overall surface area of the electrode to the geometric area of the electrode, A;

j(t) is the current density, expressed as the ratio of electrical current to the geometric area of electrode in contact with electrolyte as a function of time, t;

n is the number of exchanged electrons per molecule of gaseous reactant;

F is the Faraday constant;

$w_c$, $l_c$, and $h_c$ are the width, the length and the height of the channel;

$n_c$ is the number of channels covering the electrode;

$\alpha_{g,c}$ is the solubility of the gas in the electrolyte;

$w_m$, $l_m$, and $z_m$ are the width, length and thickness of the polymer membrane;

$\alpha_{g,m}$ is solubility of the gas in the polymer; and $P_g$ is the partial pressure of the gas in the outer atmosphere.

Thus, the ratio of the overall electrode area to the amount of gas dissolved in the electrolyte and the membrane, R, is given by the following equation:

$$R = (R_f A)/[(w_c l_c h_c n_c \alpha_{g,c} + w_m l_m z_m \alpha_{g,m}) P_g] = nF/(j(t) dt).$$

For a typical average diffusion limited current density of 1 mA/cm$^2$, n=4, and a reasonably short response time of t=1 min, the ratio R should at least amount to 6.4×10$^8$ mm$^2$/mol O$_2$. If this ratio is smaller than the minimum, the diffusion layer may still penetrate the membrane to the outer atmosphere but after a proportionally longer time. If this ratio is larger than the minimum, the outer atmosphere will be penetrated in a shorter time.

Example 5

Fluid Actuation and pH Gradient Generation

The fluid dynamics of a microfluidic electrochemical cell of Example 2 with respect to the ORR was also studied by in-situ imaging using fluorescence microscopy. The electrolyte for the fluorescence measurements was 0.1 M KCl+0.1 mM fluorescein (pH=4). The emission of this probe was used to image the spatial evolution of changes in the local pH of the electrolyte as occurred during the course of the ORR. The emission of the fluorescein in the green is one for which the quantum yield (Φ) is strongly pH dependent. For the neutral molecule, the reported value of Φ is 0.20-0.25 (Monique M. and L. Lars, *J. Luminesc.*, 1975, 10, 381). For the fluorescein monoanion (pKa=4.3), Φ is 0.25-0.35, while for the dianion (pKa=6.7), Φ is markedly larger (~0.93).

The fluorescence images were taken by using an epifluorescent upright microscope (AX-70; OLYMPUS, Melville, N.Y.) equipped with a MAGNAFIRE charge-coupled device (CCD) camera (OPTRONICS, Goleta, Calif.) and analyzed using IMAGE-PRO software (MEDIA CYBERNETICS, Inc., Silver Spring, Md.). A Hg-lamp with a BP 460-490 cutoff filter was used as UV source, while the emitted fluorescence was collected through a high pass BA515IF filter. Emission in the red, green and blue was acquired by passing the light through separate cutoff filters mounted on the CCD. In order to correct for differences in fluorescein concentration and surface heterogeneity along the microfluidic network, the fluorescence intensities were expressed as ratios of the emission intensities in the green and the red. The division was performed on a pixel-by-pixel basis.

Figure 13A:
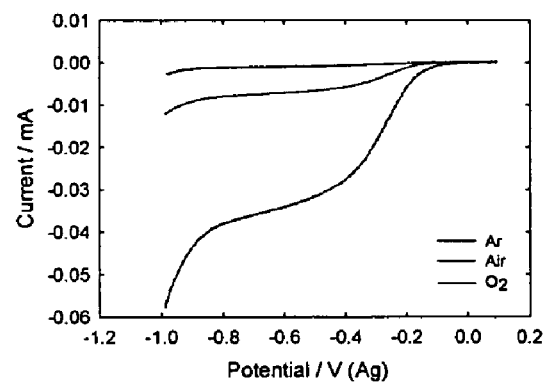
FIG. 13A is a graph of polarization curves for a microfluidic electrochemical cell in various atmospheres.
Figure 13B:
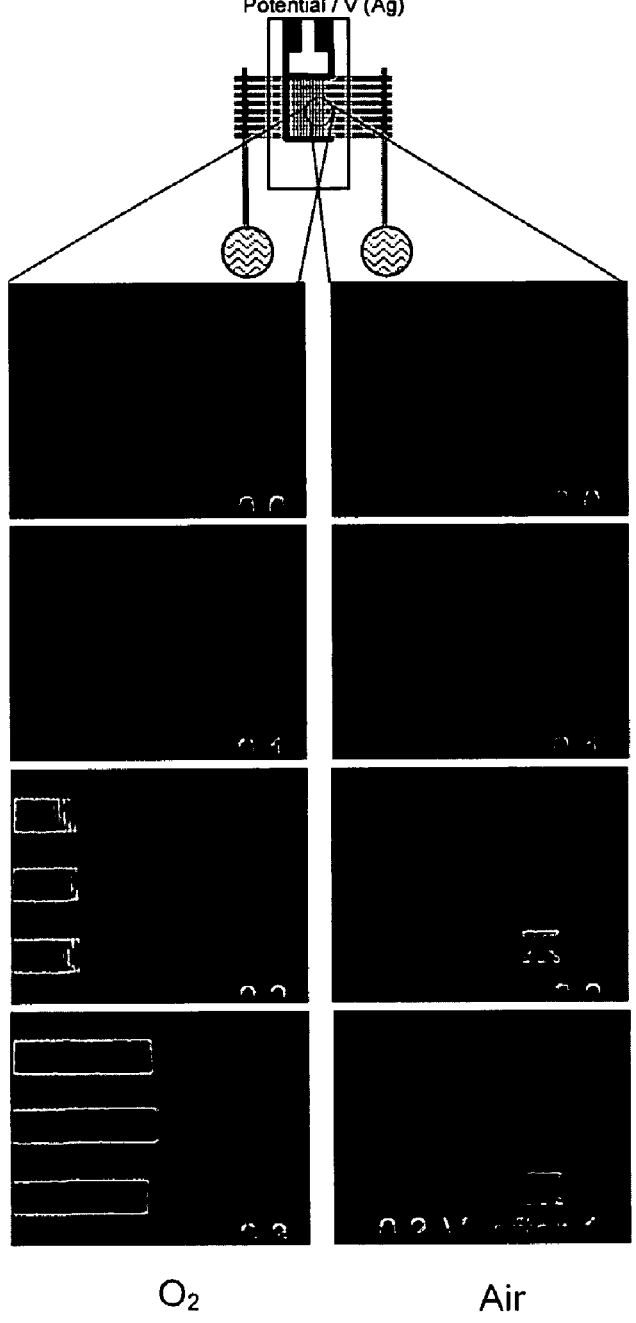
FIG. 13B is a collection of fluorescence micrograph images of the microfluidic electrochemical cell during operation.

The fluorescence micrographs shown in FIG. 13B were captured at different points during a cathodic potential scan (1 mV s$^{-1}$) from the open circuit potential (OCP) to −0.2 V. Data for scans carried out in two different gas environments are shown. Typical cathodic polarization curves recorded in argon, air, and oxygen atmospheres are shown in FIG. 13A, with the data for argon on top, the data for air in the middle, and the data for oxygen on the bottom. The specific images shown were acquired in the region of the microfluidic network where the channels intersect the Pt-IDA in an area lying closer to the reference electrode, as depicted by the schematic illustration given in FIG. 13B. During the experiment, the potential was swept from the OCP in a cathodic direction and held at 0.0V, −0.1V, −0.2V or −0.3V as indicated in the legends of FIG. 13B. The cathodic potential scan was continued after each image was acquired until the maximum holding potential was reached. The observed changes show the occurrence of substantial local changes in pH (green emission marks a significant increase in the basicity of the electrolyte). In addition, these changes show the generation of substantial fluid flow due to the Faradaic currents present at the working electrode.

When performed in unbuffered solutions, the ORR influenced the interfacial pH so that the reaction could be imaged using a pH sensitive dye. The production of hydroxide caused conversion of the indicator, in this case fluorescein, to its fluorescent form and serves as a marker of the ORR generated pH profile in the channels. The pH gradient that was generated between the IDA digits and the rest of the network drove the motion of the hydroxide ions away from the digits, resulting in deprotonation of the fluorescein molecules along the channels and increase of fluorescence intensity.

The pH of the solution under these conditions can be estimated from the ORR polarization curve by using the following equation:

$$pH = 14 + \log \frac{-\frac{dt}{dE}\int_{OCP}^{E} i\, dE}{F \times V}$$

i is the electric current;
dE/dt is the potential scan rate;
F is the Faraday constant; and
V is the volume of solution affected by the pH change.

Since the true value of V is not accurately known, the approximate pH values during the potential scan can be estimated by calculating them for two limiting cases: the first, in which the affected volume is assumed to be immediately above the electrode and the second, where the entire electrolyte volume in the channels is taken into account. For example by using the above equation it can be estimated that, by the time the potential reaches the value of −0.13 V, the pH rises from the initial value of pH=4 at the beginning of the scan to a value within of from pH=12 to pH=8 for the two limiting cases, respectively. Even when the device was operated at fairly low ORR currents (<1 μA) a dramatically high pH gradient was created between the working electrode and the remainder of the microfluidic network. At potentials lower than E=−0.13 V, the fluorescence spread beyond the geometric area of the electrode, and the fluid moved in both directions from the working electrode. Under the assumption that a linear concentration gradient is formed between the working electrode and counter electrode at a distance of approximately 1.5 cm, one can estimate that for a difference of at least 8 pH units by the end of the potential scan (pH=12 at the working electrode and pH=4 at the counter electrode and the working electrode) and a hydroxide ion diffusion coefficient of D=5.3×10$^{-5}$ cm$^2$/s(ref), a diffusion flux, φ, of φ=3.5×10$^{-7}$ mol OH$^-$/(cm$^2$×s) is being generated capable of dragging 0.1 nmol/s of water (assuming a hydration number for hydroxide ions, h, of h=3), which corresponds to 1.8 pL H$_2$O/s being displaced by pure diffusion in both directions from the working electrode.

The fluid was driven more strongly toward the counter electrode (CE, left) than toward the reference electrode (RE, right), an effect which was more pronounced for channels that are located closer to the two reservoirs. The latter can be attributed to several phenomena which are likely to take place when electrochemical reactions are being performed in confined spaces.

The first factor is the higher pH gradient generated between the working electrode and the counter electrode than between the working electrode and the reference electrode, due to the oxygen evolution reaction taking place at the counter electrode. Since the pH gradient spreads over a longer distance for channels that are spaced further from the counter electrode (by 0.2 mm for each channel) the fluid moves slower toward the counter electrode in the channels that are located further upstream. In the more distant channels the motion in the opposite direction becomes more pronounced and the fluid moves faster toward the reference electrode. It should be pointed out that at the end of the potential scan, a dramatic difference in color between the liquid in the two reservoirs was observed—from pale yellow in the electrolyte corresponding to a highly acidic solution within the counter electrode reservoir, to a bright green color corresponding to the fluorescein dianion present in highly basic solution in the reference electrode reservoir.

The second factor is the contribution to the flow caused by the electrical current that passes between the working electrode and the counter electrode. As can be seen by the laminar flow profiles in FIG. 13, frames a) through d), this effect is already pronounced at very low ORR currents and can be viewed as a current driven flow. For ORR currents, i<1 μA, by using $\phi=i/(F\times A)$ where $\phi$-diffusion flux of hydroxide ions, F—Faraday constant and A—cross sectional area of the channels, one can estimate that $\phi=10^{-7}$ mol OH$^-$/(cm$^2$×s) is driven by the current, and taking into account the hydration number for hydroxide ions of h=3, it can be estimated that the passage of the electrical current is capable of dragging 0.5 pL/s of water (18 nL for 1 h).

The third factor is the contribution to the electrophoretic flow caused by the unequal electric fields imposed on the ions in the two opposite directions from the working electrode. Due to the relatively high electrical current passing between the working electrode and counter electrode during the potential scan (1-10 μA) and the high Ohmic resistance in the channels (≈0.5 MΩ), the voltage between the working electrode and counter electrode can reach almost fivefold higher values than the voltage between the working electrode and reference electrode (5 V vs. 1 V) causing the ions to move faster in the direction of the counter electrode. The electrophoretic mobilities of H$^+$ (36.25×10$^{-4}$ cm$^2$/(V×s)) and for OH− (20.50×10$^{-4}$ cm$^2$/(V×s)) translate to a electrophoretic linear velocity of 122 μm/s for the migration of H+ from the counter electrode to the working electrode and to 68 μm/s for the migration of OH− from working electrode toward the counter electrode for a voltage of 5 V and a distance between the working electrode and the counter electrode of 1.5 cm. The net electrophoretic flow should therefore induce a net hydraulic flow from the counter electrode to the working electrode reservoir.

Figure 14:
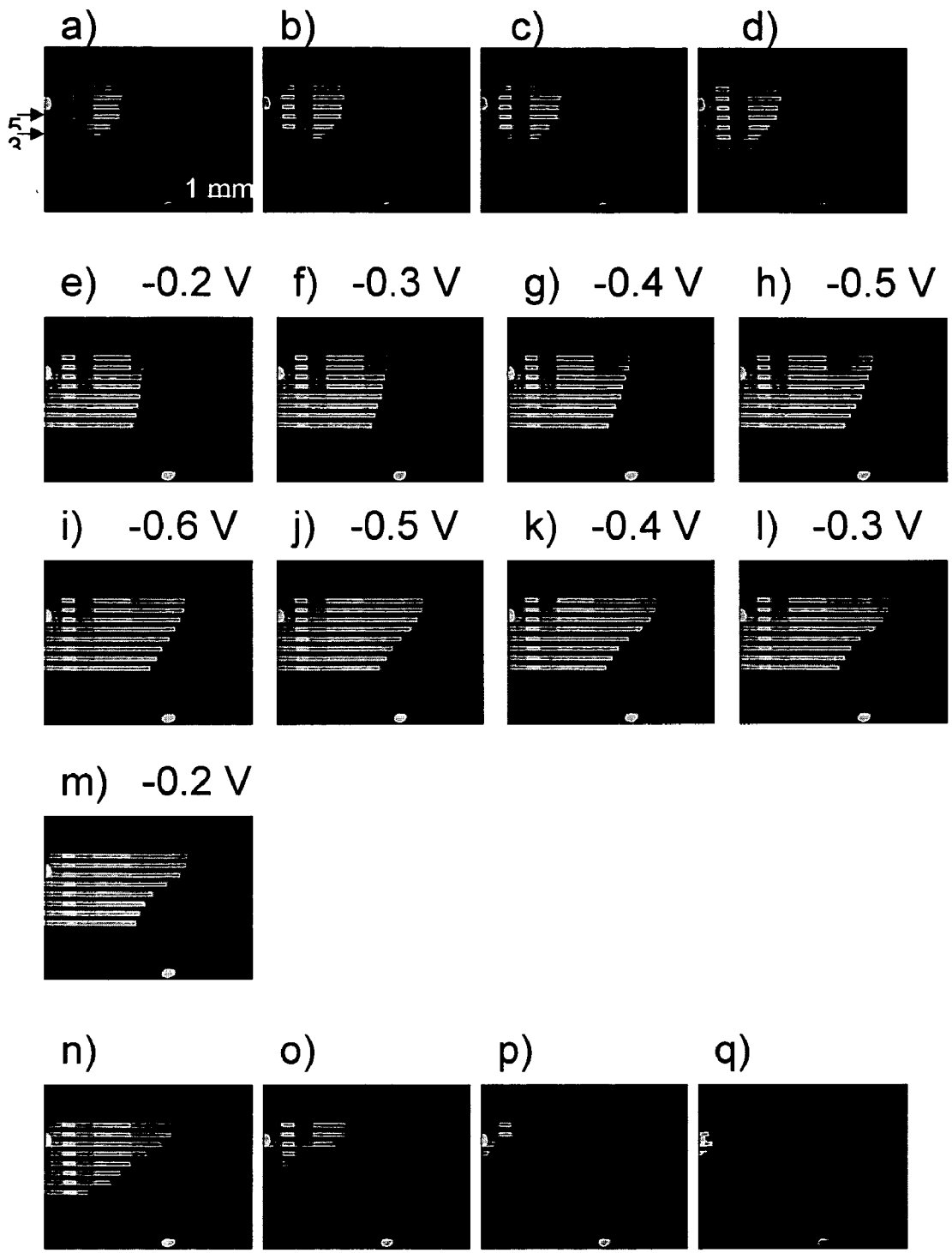
FIG. 14 is a collection of fluorescence micrograph images of a microfluidic electrochemical cell during operation.

Referring again to FIG. 14, the images taken at constant potential (E=−0.1 V) during 5 min (frames a-d) revealed that when the device was operated at low ORR currents, the fluid flowed solely in one direction toward the counter electrode. Under these conditions, a stable laminar flow profile developed, characteristic of a pressure driven flow, suggesting that at −0.1 V the fluid was continuously being pumped from one reservoir (reference electrode) to another (counter electrode). As the potential was scanned further in the cathodic direction (frames e-i), the laminar profile disappeared as the ORR currents increased and the hydroxide ions began to diffuse toward the reference electrode, thereby suppressing the drag of fluid toward the counter electrode. Consequently, the electrolyte was being pumped in the opposite direction. Following the potential scan, continuous pressure driven flow was recorded at an average linear velocity of 10 μm/s translated to a volumetric flow rate of 0.1 nL/s for around 15 min (frames n-q), which corresponded to an overall amount of 90 nL being displaced from one reservoir (counter electrode) to another (reference electrode).

It should be noted that the fluid flow in the microfluidic electrochemical reactor system was different from the electroosmotic flow normally observed in capillary electrophoresis, as the former was caused by the diffusion of the species generated by the electrochemical reaction and by the high electrical current that passed through the microfluidic channels, while the latter is driven by the surface charge at the walls of the capillary. Even though the electrochemically generated flow rates were considerably lower than typical electroosmotic flow rates (nL/s vs. mL/s), the power requirements for the former are dramatically reduced (5 V vs. 10 kV).

Example 6

Microfluidic Fuel Cell Containing Platinum Electrodes

Soft lithography methods were used to fabricate a device similar to that shown in FIG. 7. Two 1.23 mm$^2$ platinum electrodes were fabricated by e-beam evaporation of platinum onto a photoresist pattern fabricated on quartz (see Example 1). After removing the photoresist, the electrode array was embedded into PDMS such that the electrodes were spaced 1 cm apart. Microfluidic channels that were 200 μm wide, 200 μm apart and 70 μm high were fabricated by replicating a photoresist-derived master. The 2 cm wide and 1 mm thick microchannel network was placed above the electrodes leaving them sealed between the two PDMS layers. The channels were filled with electrolyte by using the capillary outgas technique. A third, 5 mm thick PDMS layer into which holes were punched to serve as leads for the fuel gases was placed onto the microchannel network with the holes positioned above the electrodes. The entire PDMS setup was placed into an argon-purged PLEXIGLAS box, which provided electrical leads for the anode, the cathode, and two silver wires serving as pseudo-reference electrodes for electrochemical studies as well as nozzles for inlet and outlet of the feed gases. After purging the chamber with argon for 1 h, hydrogen was fed to the anode gas-supply reservoir and oxygen similarly to the cathode.

Figure 15:
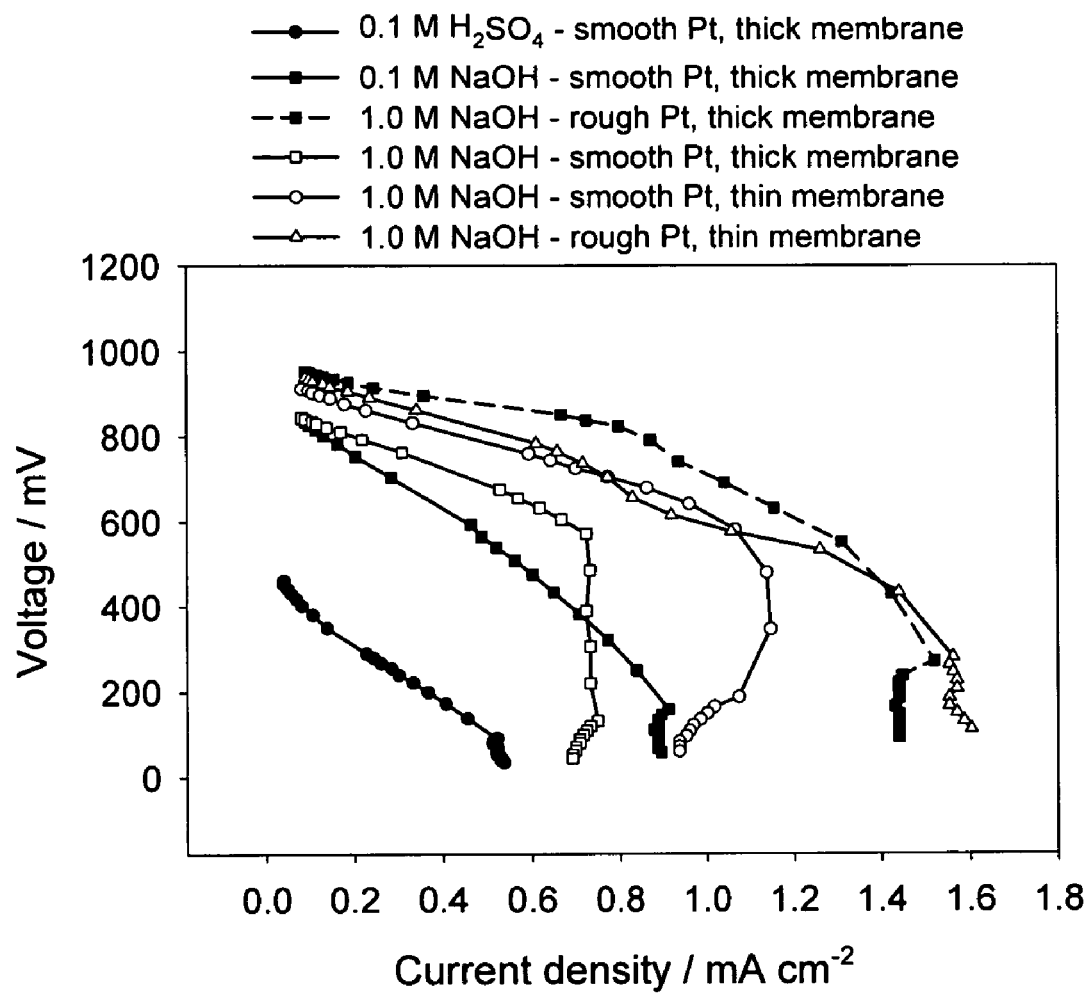
FIG. 15 is a graph of polarization curves for a $H_2$—$O_2$ microfluidic fuel cell.

FIG. 15 shows a series of representative polarization curves recorded by taking the current and voltage readings of the cell for imposed resistances in the range from 1 kΩ-900 kΩ. Several electrolytes were used in the study of the device performance including 0.1 M H$_2$SO$_4$, 1.0 M NaOH and 0.1 M NaOH. The polarization curves in FIG. 15 and the power density plots presented in FIG. 16 demonstrate that the H$_2$—O$_2$ fuel cell can be operated at high current densities even in the absence of an anode/cathode membrane separator by taking advantage of the selective feed of gases toward the electrodes of interest.

Figure 16:
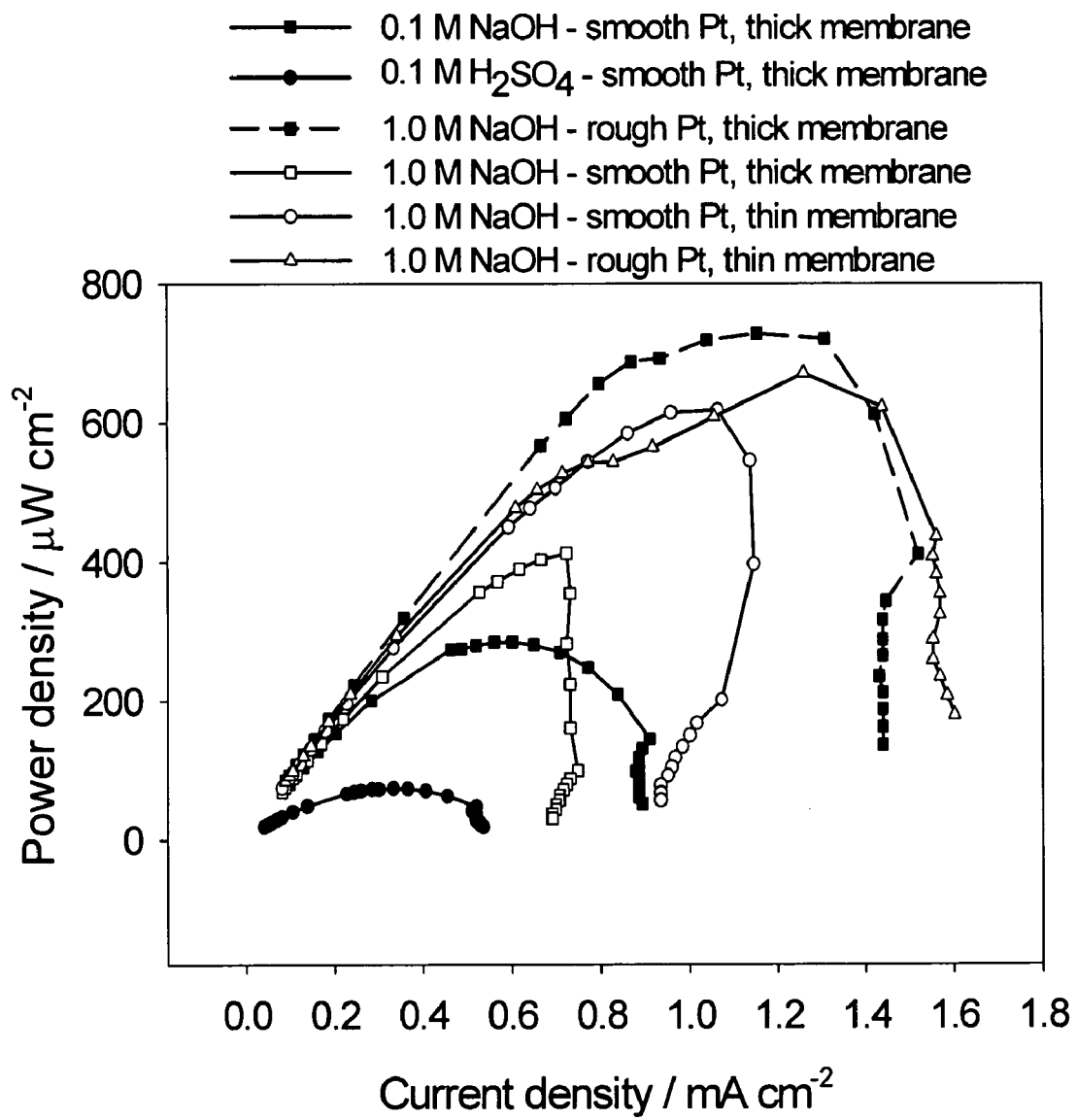
FIG. 16 is a graph of power density curves for a $H_2$—$O_2$ microfluidic fuel cell.

The data in FIGS. 15 and 16 show several important features relevant to the performance of the device. First, the use of a basic supporting electrolyte (0.1 M NaOH vs. 0.1 M H$_2$SO$_4$) resulted in both a higher open circuit potential (900 mV vs. 640 mV) and larger limiting current density (0.9 mA/cm$^2$ vs. 0.5 mA/cm$^2$). These differences both appeared to correlate with expectations of device character limited by the kinetics of the cathode. This was shown by the performance of devices constructed using electrochemically roughened Pt anodes and cathodes. In a representative example, a literature protocol was used to generate Pt electrodes with roughness factors, R$_f$, exceeding 90. As shown in FIG. 16, these devices produced much higher limiting current densities (1.4 mA/cm$^2$) and the performance, as noted by comparisons of the power density plots, showed that their maximum power output was higher and was reached at higher current densities.

In addition, the latter data clearly reveal that the PDMS gas exchange membrane did not limit the sustainable currents of the device over its full range of operation, as an increase in electrode area led to improved performance. The current densities realized in this fully passive microfluidic fuel cell design exceeded those obtained in dynamic systems. For example, a direct formic acid fuel cell that uses multi-stream laminar flow was recently reported to have obtained a maximum current density of 0.8 mA/cm². These values are significantly higher than those obtained in a variety of biofuel cells that utilize enzymes as selective catalysts. The microfluidic cell of this example operated at room temperature with maximum power density of around 700 µW/cm².

Figure 17:
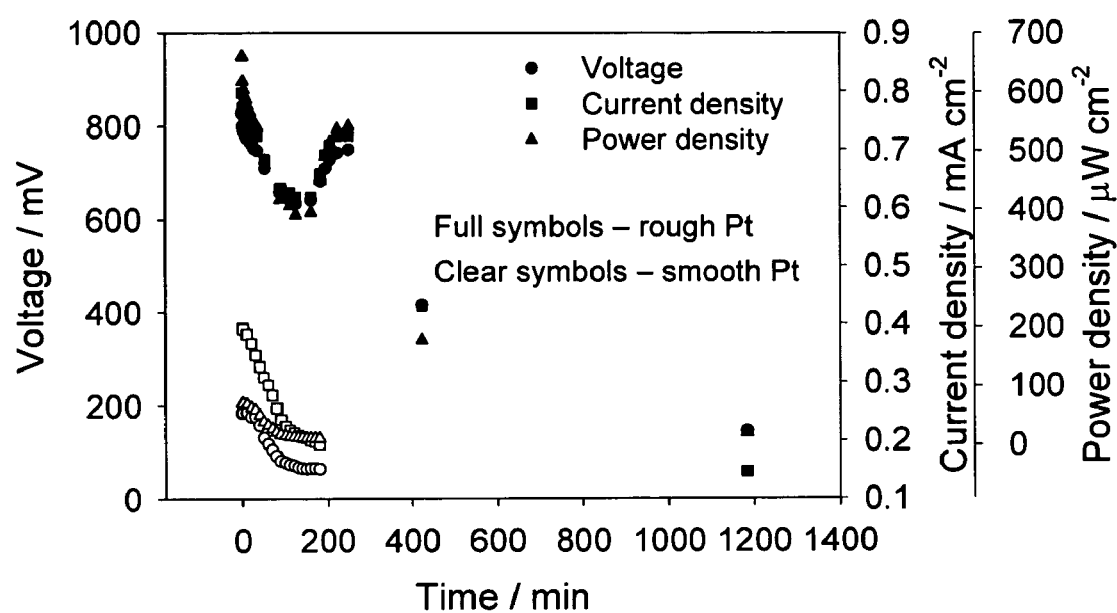
FIG. 17 is a graph of the time dependency of voltage, current density and power density for a microfluidic fuel cell.

The cell design used in this study purposely omitted an integrated anode/cathode separator. The stability and lifetime of the device was limited therefore by the rate at which crossover depolarizes the cell. FIG. 17 shows that when the cell operated continuously at maximum power for 3 h, it lost almost 75% of its power in the first 1.5 h after which the observed currents stabilized. The performance stability is markedly improved for cells based on high surface area electrodes. The filled symbols in the plots correspond to data for roughened electrodes, whereas the empty symbols correspond to the smooth electrodes. The diffusive mixing of the gases within the electrolyte as well as in the PDMS membrane layer can be limited by a variety of adjustments. For example, the electrode surface areas may be tailored to minimize the reaction of the undesired reactant. In another example, a thicker PDMS membrane above the anode would compensate for the differences in the gas permeation rates as needed to suppress the hydrogen crossover to the cathode. In another example, placing an ionomer separator membrane such as NAFION between the two compartments inside the channels would also serve to prevent such crossover. The Ohmic losses this would induce inside the channels can be reduced easily by fabricating wider channels. Employing more complex microchannel networks could enable continuous fluid flow selectively above the electrodes, which would further improve the convective transport of the feed gases toward the electrode surfaces.

Example 7

Microfluidic Fuel Cell Containing Platinum Cathode and Palladium Anode

Platinum (Pt) electrodes were fabricated as described in Example 1. These electrodes were platinized at −0.5 V (Ag/AgCl) for 30 s in 3% wt. $H_2PtCl_6 \times 6H_2O$ (ALDRICH, Milwaukee, Wis.)+x % Pb-acetate (ALDRICH) aqueous solution in a conventional three-compartment electrochemical cell, using a Pt-wire auxiliary as the counter electrode and an Ag/AgCl reference electrode. An electrical contact between the fabricated Pt working electrode and the potentiostat was made via a Pt wire attached to the electrode by silver-epoxy resin (EPO-TEK 4110). The contact was then insulated with nail-polish, such that only the fabricated electrode was exposed to the electrolyte for platinization. Two different concentrations of Pb-acetate were used in the platinization. The higher concentration (0.3%) resulted in a larger surface area and was used as the cathode. The lower concentration (0.3%) resulted in a smaller surface area and was used to prepare the anode.

The anode was prepared by electrochemically "activating" the platinized-Pt electrode by potential cycling from −0.225 V to 1.25 V vs. Ag/AgCl at 5 mV s$^{-1}$ in 0.5 M $H_2SO_4$ for 12 cycles. At the point when the potential reached the Pt double layer region in the positive ongoing sweep, the electrode was taken out of the cell, transferred to a de-aerated 0.1 M $H_2SO_4$+5 mM $Pd(NO_3)_2$ (STREM CHEMICALS, Newburyport, Mass.) solution, where Pd was spontaneously deposited for 5 min. The electrode was then taken out of the palladizing solution, rinsed well with ultrapure water, returned to the electrochemical cell and treated by potential cycling from −0.225 V to 0.6 V vs Ag/AgCl at 5 mV s$^{-1}$ in 0.5 M $H_2SO_4$ until a stable cyclic voltammogram was obtained (usually 2-3 cycles). The described procedure was carried out 3 times to yield a Pd/Pt anode rich in palladium.

The microfluidic network was prepared using the methods described in Example 2 to provide a network of 8 parallel channels, where the channels were 200 µm wide, 70 µm high, and were separated from each other by a distance of 200 µm. Each channel was 2 cm long, and the channels were connected at each end with a perpendicular channel having a length of 1.3 cm. A biopsy punch was used to form the holes (3 mm diameter) for filling the microfluidic network with electrolyte using the capillary outgas technique. Extension reservoirs for the platinum counter electrode and the silver reference electrode were placed on top of the holes. The entire setup was placed in a PLEXIGLAS box. Hydrogen was fed to the anode through a copper microchannel tubing (outer diameter 2 mm) which was inserted into a PDMS slab placed on top of the anode through a 3 mm wide hole that served as a lead for the hydrogen gas. The purpose of the latter was also to suppress the dissipation of the gas into the ambient and maintain the partial pressure above the PDMS membrane at its maximum.

The anode and the cathode were electrically connected via a decade resistor and the polarization curves of the fuel cell were monitored by varying the resistance in the range from 1 kΩ-900 kΩ and by measuring the voltage and the current using digital voltmeters. The current densities were calculated with respect to the geometric surface area of the electrode in contact with the electrolyte (0.012 cm²). The roughness factor, $R_F$, of the Pt cathode was estimated to be $R_F=300$. The surface area of the anode was designed to be smaller than that of the cathode in accordance with the fact that the hydrogen oxidation reaction (HOR) is orders of magnitude more facile than the ORR. By keeping the deposition parameters (potential, time) equal to the ones used for the fabrication of the cathode and using smaller amounts of Pb-acetate in the platinizing solution, a platinized-Pt support of a roughness factor of $R_F=43$ was obtained.

Figure 18:
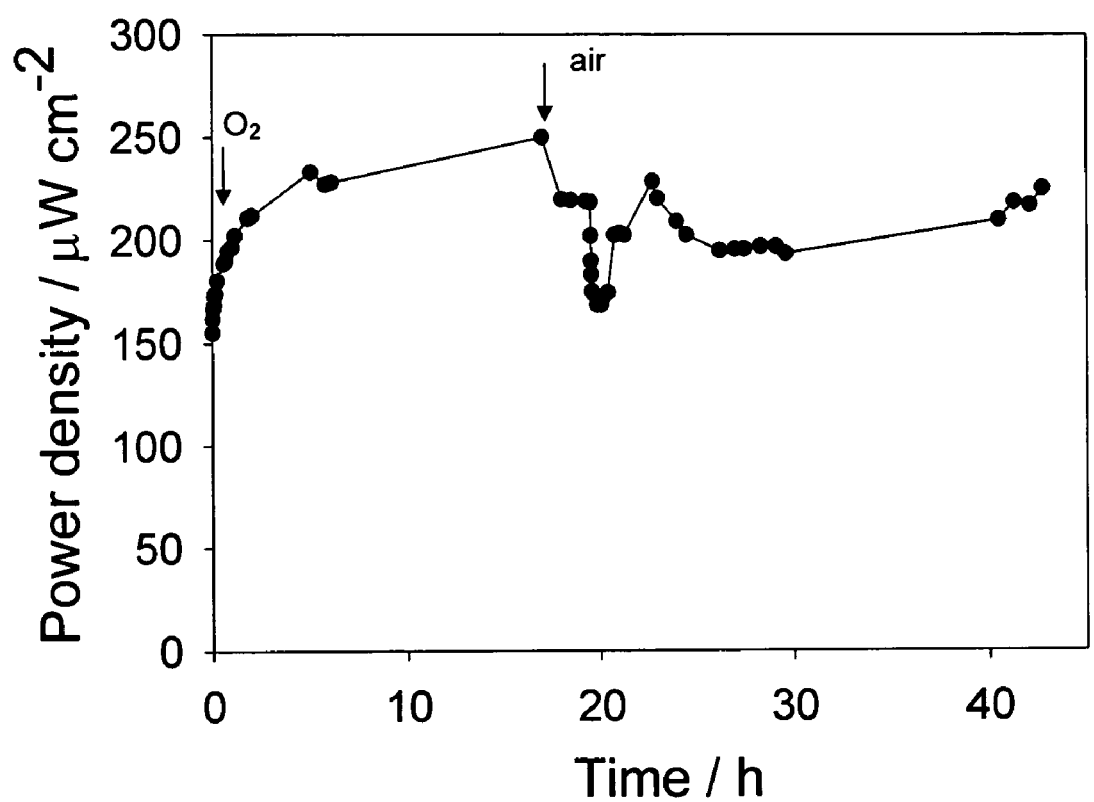
FIG. 18 is a graph of power density versus time for a hydrogen-oxygen and hydrogen-air microfluidic fuel cell.

The temporal stability of the fuel cell was first tested in 5 M $H_2SO_4$ with using hydrogen and oxygen as fuels being supplied to the electrodes via microchannel tubings. The voltage and current measurement was carried out under a cell load of R=80 kΩ, starting at 5 min after the gases had been introduced to the electrodes. As seen from the graph in FIG. 18, the temporal stability of the microfluidic fuel cell was markedly improved compared to the microfluidic fuel cell of Example 6, in which both the electrodes were platinum. While the latter depolarized fairly rapidly, the former was found to operate stably during the entire measurement (around 43 hours). Moreover, the graph in FIG. 18 reveals that the performance of the device was practically unaffected by the oxygen partial pressure at the cathode. Upon switching the atmosphere at the cathode from oxygen to ambient air, the power density initially decreased (seen by the "dip" in the plot of FIG. 18), after which it increased and stabilized at a value that was almost equal to the one measured in pure oxygen (≈200 µW cm$^{-2}$). During the remaining 20 hours of the experiment, the power density of the system was not seen to exhibit significant variations.

Figure 19A:
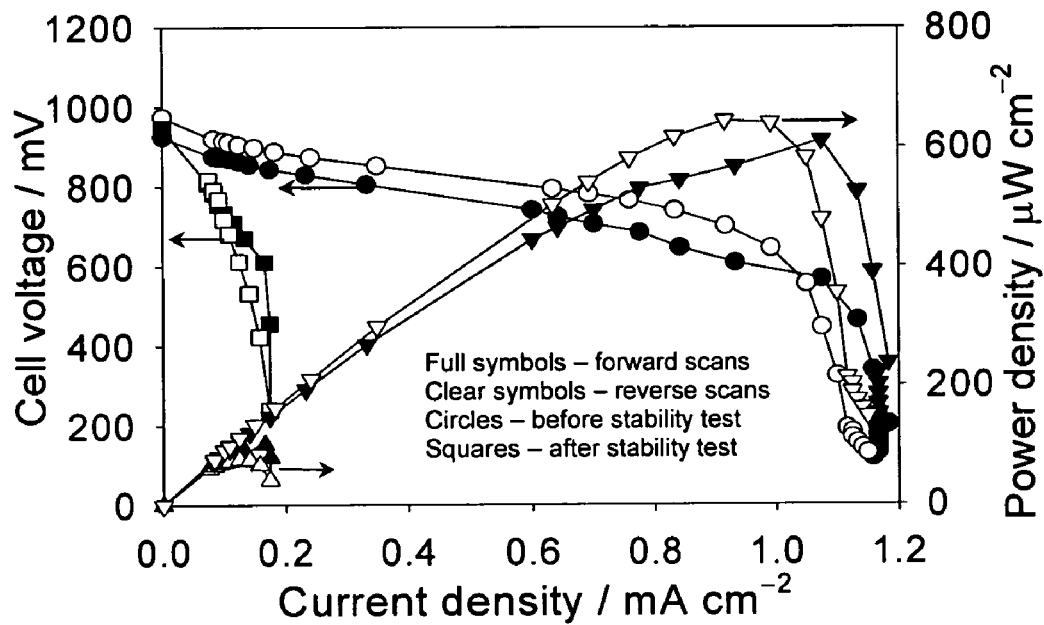
FIG. 19A is a graph of polarization curves and of power density versus current density for a hydrogen-air microfluidic fuel cell in 2.5 M NaOH.
Figure 19B:
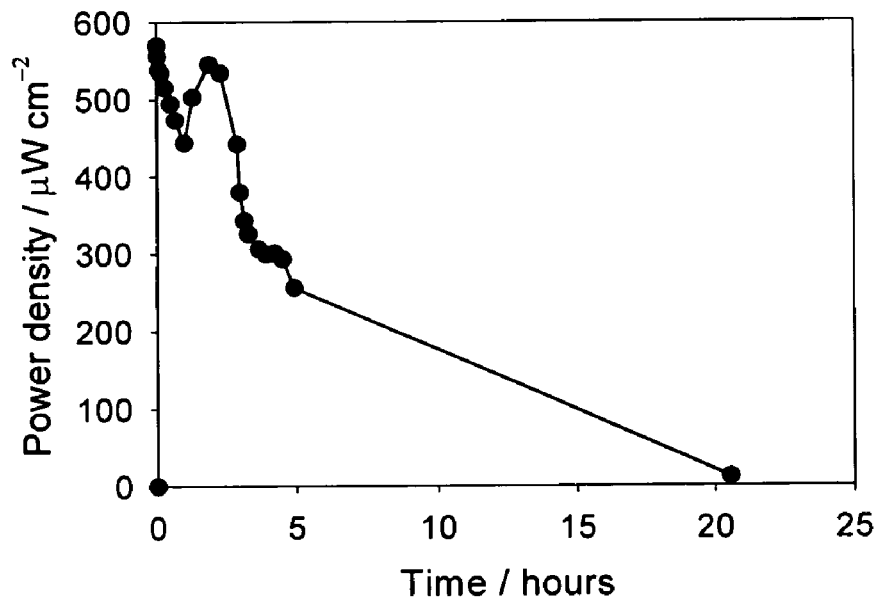
FIG. 19B is a graph of power density versus time for the microfluidic fuel cell 2.5 M NaOH.

The performance of the device was found to be markedly different when the cell operated in 2.5 M NaOH. For these experiments, the acidic electrolyte in the microfluidic network was replaced by 2.5 M NaOH via hydrodynamic flow through the channels induced by keeping the electrolyte levels in the two reservoirs at uneven heights. During this time, the cell was left under open circuit conditions. When the open circuit voltage of the cell stabilized (at OCV=925 mV), the polarization curves of the device in the direction of increasing and decreasing current densities were measured. FIG. 19A shows these data, together with the corresponding power density versus current density plots. As seen from the graph in FIG. 19B, when the device operated in basic solutions for longer times, the cell rapidly depolarized. Though the cell output power measured in the beginning of the measurement was larger than the one recorded in an acid (550 $\mu W\ cm^{-2}$ vs 250 $\mu W\ cm^{-2}$), the cell lost approximately 50% of its power within the first 4 hours, after which it fully depolarized during the subsequent 17 hours of operation. The polarization curve measured after the stability test is shown in FIG. 19A, showing that the device produced substantially lower current densities under these conditions.

The loss of cell power in 2.5 M NaOH was possibly caused by the formation of insoluble carbonate precipitates at the electrodes. During cell flushing with 5 M $H_2SO_4$, carried out after the device had fully depolarized in 2.5 M NaOH, gas bubbles likely originating from carbon-dioxide being released by carbonate dissolution in the channels were seen to come out of the microfluidic network in the direction of the fluid flow. Moreover, the polarization curves measured after the stability test (green in FIG. 19A) showed that the OCV of the fuel cell remained practically unchanged by the depolarization process, indicating that the latter was most probably caused by physical blockage of the electrode(s) area electrode and not by "poisoning" or reagent crossover, as the latter effects would have caused a decrease in the OCV of the device. More importantly, an acid flush procedure resulted in full recovery of the device operation characteristics, as evidenced by the polarization curves and the stability test data presented in FIG. 20.

Figure 20A:
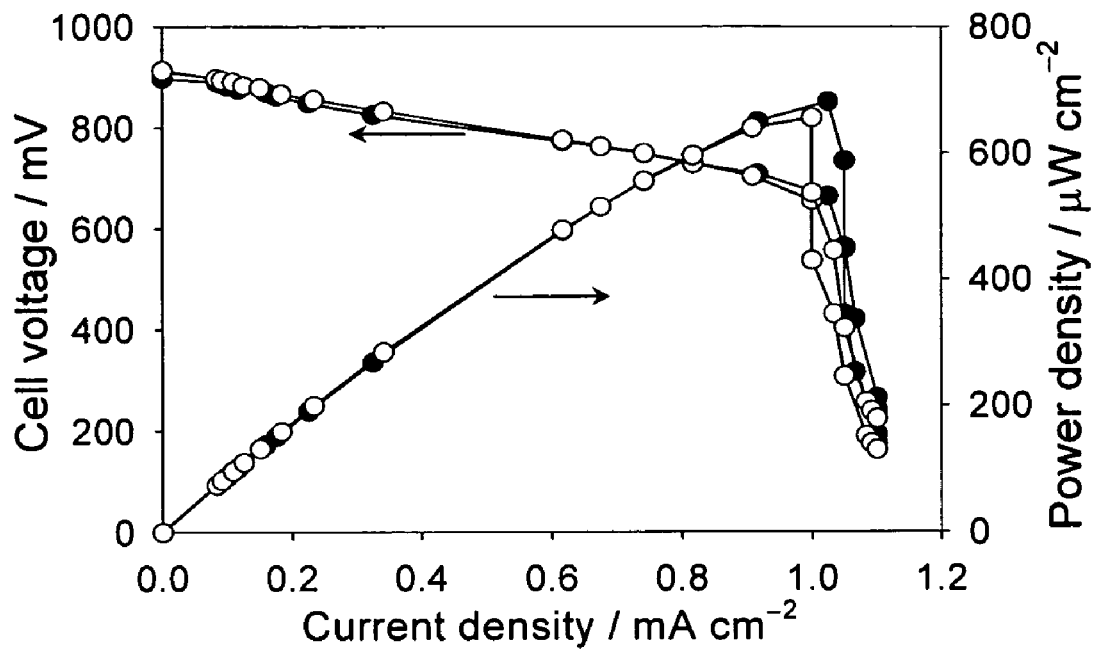
FIG. 20A is a graph of polarization curves and of power density versus current density for a hydrogen-air microfluidic fuel cell in 5 M $H_2SO_4$.
Figure 20B:
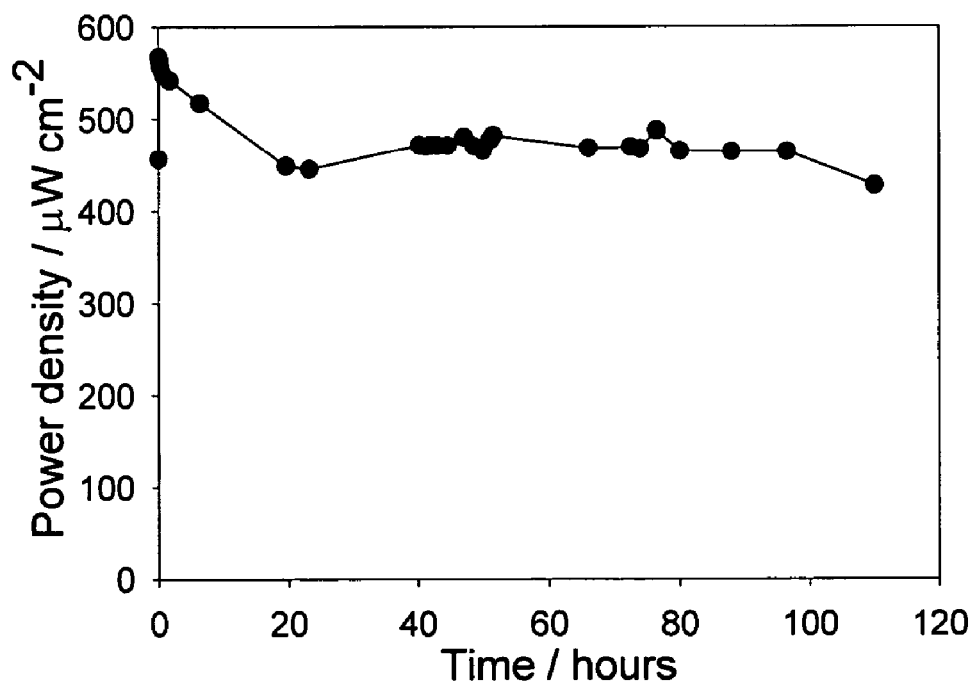
FIG. 20B is a graph of power density versus time for the microfluidic fuel cell in 5 M $H_2SO_4$.

Due to the fact that further formation of insoluble carbonate species was suppressed in acidic solution, the temporal stability of the fuel cell dramatically improved compared to the one observed in 2.5 M NaOH. Shown in FIG. 20A is a result of a long-term stability test that was performed in 5 M $H_2SO_4$ under a constant load of R=80 k$\Omega$. The plot in FIG. 20B reveals that after an initial decrease of cell power density from 570 $\mu W\ cm^{-2}$ to 450 $\mu W\ cm^{-2}$ during the first 20 hours of device operation, the hydrogen-air fuel cell continued to operate at almost constant power density of around 480 $\mu W\ cm^{-2}$ for >100 hours, exhibiting no significant variations in output power during this time.

During the entire time of cell operation in 5 M $H_2SO_4$, no electrolyte was being added or removed from the reservoirs, revealing that the water being generated during the operation of the fuel cell was evaporating from the microfluidic structure at a rate that closely resembled the one of its generation. The evaporation most probably took place directly into the ambient from the extension reservoirs and/or by permeation through the PDMS membrane. Nonetheless, no water management system was needed to sustain the stable performance of the device.

Example 8

Microfluidic Fuel Cell Utilizing Formic Acid Oxidant

A microfluidic fuel cell was fabricated as described in Example 7, except that the oxidant fed to the anode was formic acid. Formic acid was stored in a reservoir made of PDMS and supplied to the anode by diffusion through the PDMS membrane on the microfluidic channels. The anode and the cathode were electrically connected via a decade resistor and the polarization curves of the fuel cell were monitored by varying the resistance in the range from 1 k$\Omega$-900 k$\Omega$ and by measuring the voltage and the current using digital voltmeters. The current densities were calculated as described in Example 7.

Figure 21:
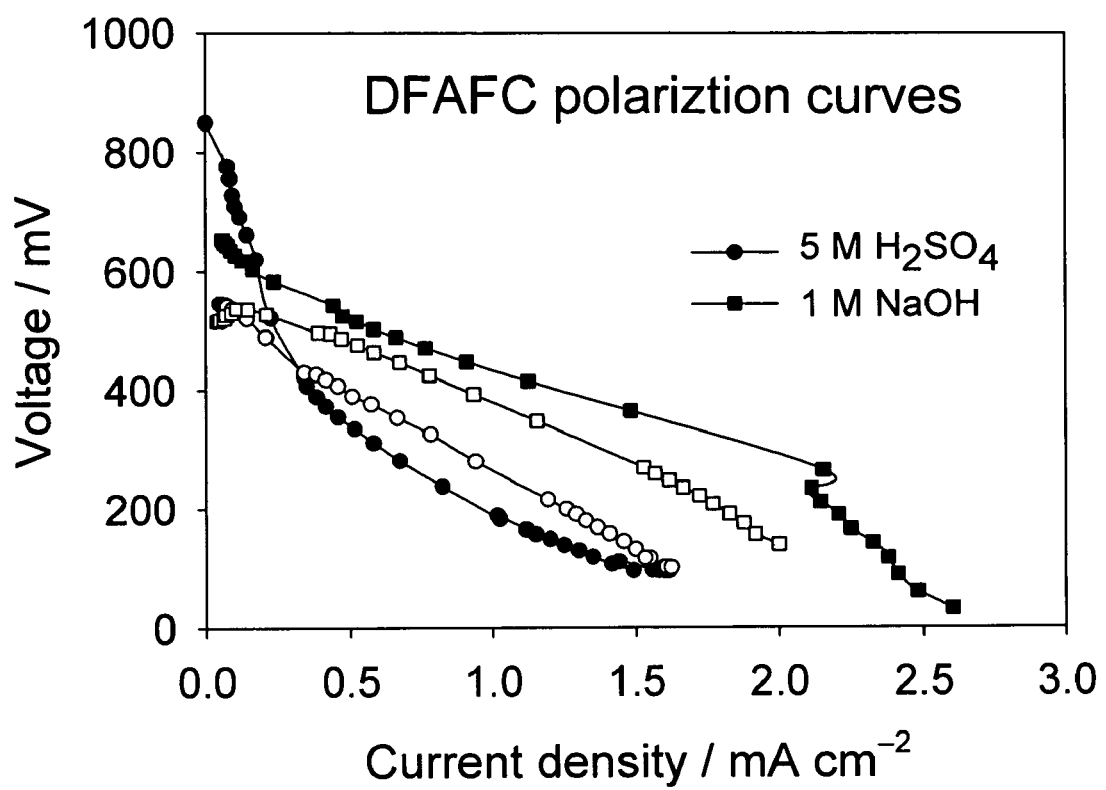
FIG. 21 is a graph of polarization curves for a formic acid microfluidic fuel cell.
Figure 22:
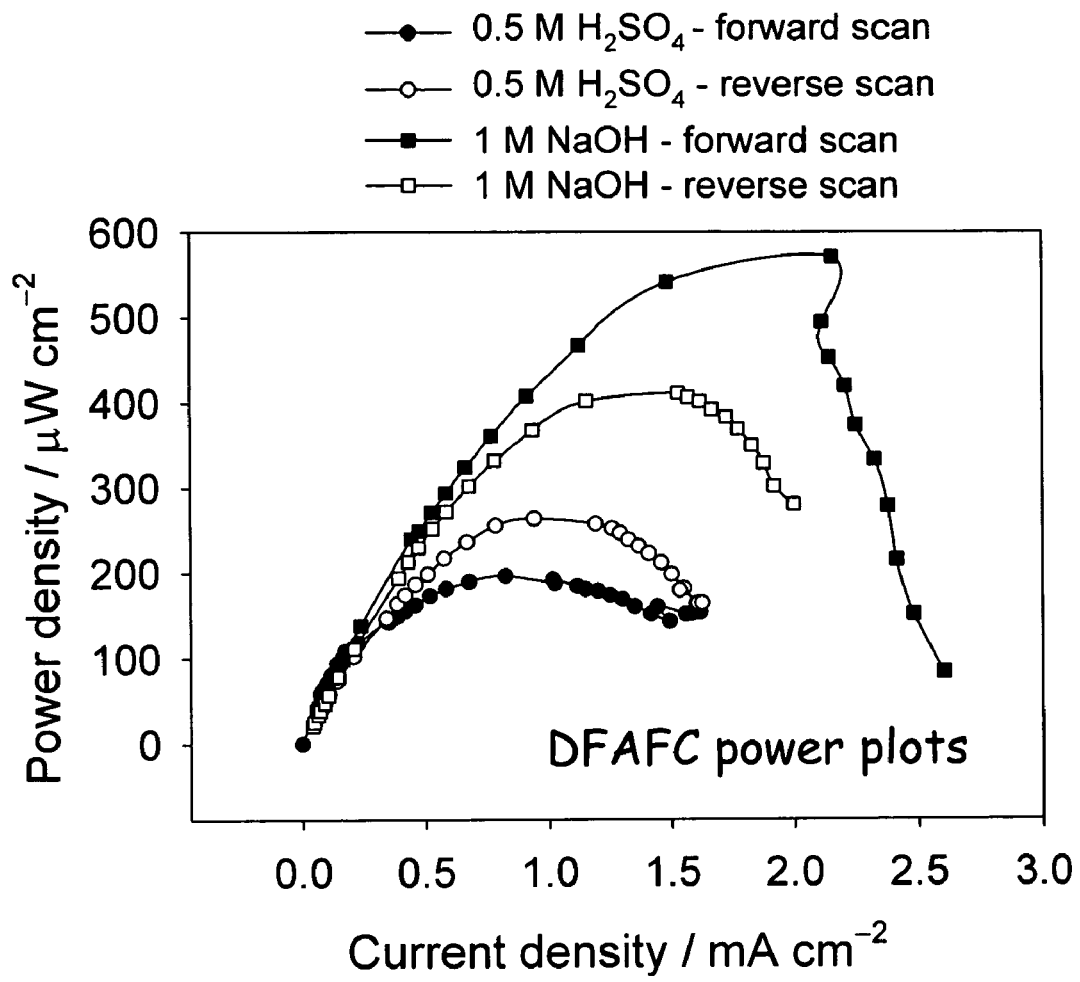
FIG. 22 is a graph of power density versus time for a formic acid microfluidic fuel cell.
Figure 23:
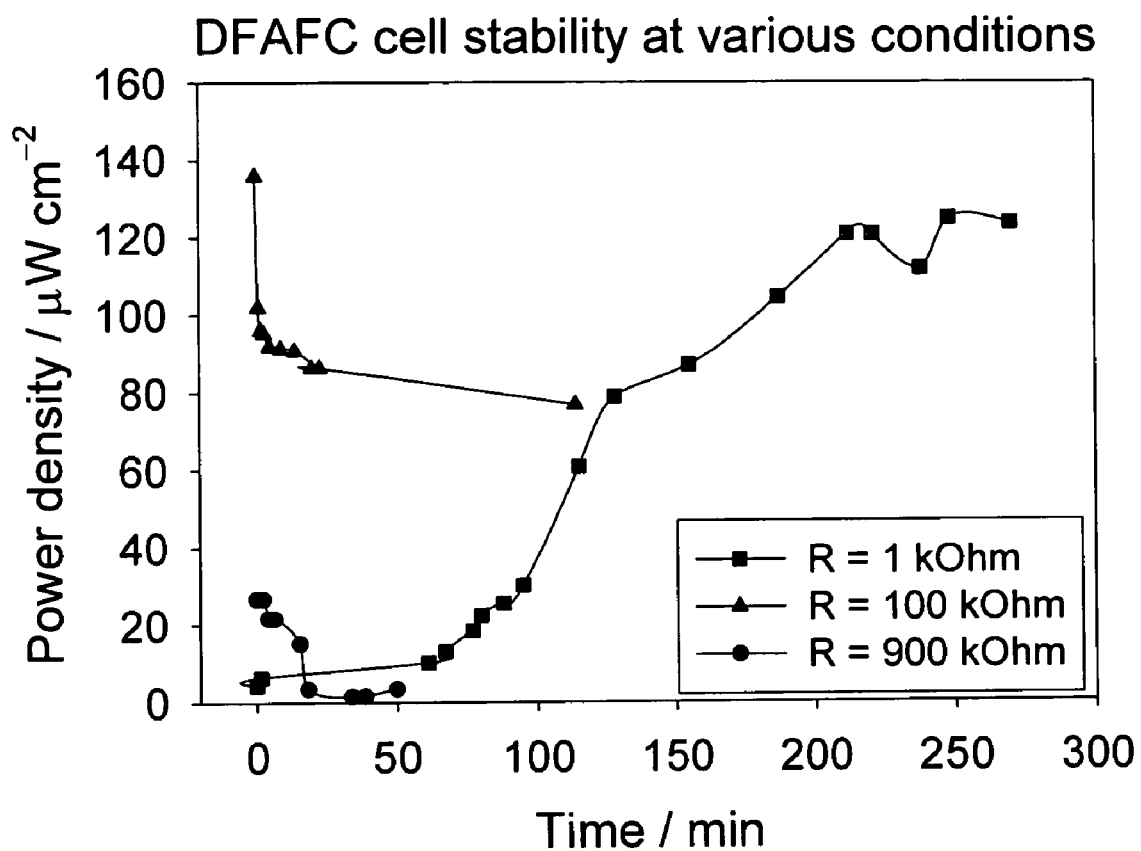
FIG. 23 is a of power density versus time for a formic acid microfluidic fuel cell.

FIG. 21 shows a series of representative polarization curves recorded by taking the current and voltage readings of the cell for imposed resistances in the range from 1 k$\Omega$-900 k$\Omega$. FIG. 22 shows the corresponding power density versus current density plots. The electrolytes used were 5 M $H_2SO_4$ and 1 M NaOH. The performance of the formic acid microfluidic fuel cell in basic solution was somewhat better initially, but the cell depolarized rapidly in this electrolyte. The lower performance in acid solution was likely due to the non-optimization of the cathode in acidic electrolyte. FIG. 23 shows the stability test data for the formic acid fuel cell using the acidic electrolyte of 5 M $H_2SO_4$. At low resistances (R=1 kOhm), and therefore high current densities, the power density of the fuel cell increased with time, stabilizing after approximately 3 hours. At high resistances (R=900 kOhm), and therefore low current densities, the power density of the fuel cell decreased with time, and almost completely depolarized within 20 minutes. At moderate resistances (R=100 kOhm), and therefore moderate current densities, the performance of the fuel cell was stable. Under these conditions, the power density slowly decreased with time after an initial drop.

The performance of this exemplary microfluidic formic acid fuel cell seemed to indicate a limitation due to crossover and poisoning of the cathode. Stabilization of the device would likely be accomplished by using a selective cathode that is active in the oxygen reduction reaction and inactive for formic acid oxidation. Examples of selective cathode materials include gold (Au), metal oxides, and platinum alloys such as Pt—Fe, Pt—Co or Pt—Ni. Placing an ionomer separator membrane such as NAFION between the two compartments inside the channels would also serve to prevent such crossover.

While various embodiments of the invention have been described, it will be apparent to those of ordinary skill in the art that other embodiments and implementations are possible within the scope of the invention. Accordingly, the invention is not to be restricted except in light of the attached claims and their equivalents.

What is claimed is:

1. An electrochemical reactor, comprising:
    an electrode;
    a layer comprising at least one hollow microfluidic channel on the electrode;
    a membrane comprising a gas permeable polymer on the microfluidic channel; and
    an electrolyte in the microfluidic channel;
    wherein the distance between the electrode and the membrane is less than or equal to 500 microns;
    wherein a gaseous reactant is dissolved in the electrolyte and the membrane, and the electrode comprises a surface area that is exposed to the microfluidic channel; and
    wherein the ratio of the surface area in square millimeters to the amount of dissolved gaseous reactant in moles is from $3.0 \times 10^9$ to $3.0 \times 10^{12}$.

2. The electrochemical reactor of claim 1, wherein the distance between the electrode and the membrane is from 1 micron to 500 microns.

3. The electrochemical reactor of claim 1, wherein the microfluidic channel comprises side walls extending between the electrode and the membrane, and the distance between the side walls is from 1 micron to 1 millimeter.

4. The electrochemical reactor of claim 1, wherein the hollow microfluidic channel is at least two microfluidic channels and the microfluidic channels are a portion of a microfluidic network.

5. The electrochemical reactor of claim 4, wherein the microfluidic channels are separated by a distance from 1 micron to 1 millimeter.

6. The electrochemical reactor of claim 4, wherein the microfluidic channels are separated by a distance of from 50 microns to 300 microns.

7. The electrochemical reactor of claim 1, wherein the membrane has a thickness from 1 micron to 2 millimeters.

8. The electrochemical reactor of claim 1, wherein the gas permeable polymer is selected from the group consisting of silicon-containing polymers, fluorinated polymers, polypropylene, and polymers comprising diene monomer units.

9. The electrochemical reactor of claim 1, wherein the gas permeable polymer comprises a permeability coefficient at 0° C. and $1.013 \times 10^5$ Pa pressure for at least one gaseous species of at least $5 \times 10^{-13}$ cm$^3$ cm/ cm$^3$ s Pa.

10. An electrochemical device, comprising:
the electrochemical reactor of claim 1; and
a second electrode in electrochemical communication with the electrode of the reactor.

11. The electrochemical device of claim 10, wherein the electrochemical reactor and the second electrode are on a substrate, and the microfluidic channel extends from the electrochemical reactor to the second electrode.

12. The electrochemical device of claim 11, wherein the application of an electric potential to the electrode of the reactor causes a pH gradient to form along the microfluidic channel.

13. A microfluidic electrochemical sensor, comprising:
the electrochemical reactor of claim 1, wherein the electrode of the reactor is a working electrode; and
a counter electrode in electrochemical communication with the working electrode.

14. The microfluidic electrochemical sensor of claim 13, further comprising a reference electrode in electrochemical communication with the working electrode and the counter electrode.

15. The microfluidic electrochemical sensor of claim 13, wherein the application of an electric potential to the working electrode causes an electrical current to flow between the working electrode and the counter electrode, such that the magnitude of the electrical current is related to the concentration of oxygen in an environment in contact with the membrane.

16. A microfluidic actuator, comprising:
the electrochemical reactor of claim 1; and
a second electrode in electrochemical communication with the electrode of the reactor through the at least one microfluidic channel;
wherein the application of an electric potential to the electrode of the reactor causes a net flow of electrolyte along the channel.

17. The microfluidic actuator of claim 16, further comprising a reference electrode in electrochemical communication with the electrode of the reactor and the second electrode.

18. A microfluidic fuel cell, comprising:
a first electrochemical reactor of claim 1;
a second electrochemical reactor, in electrochemical communication with the first electrochemical reactor and comprising a second electrode, at least one microfluidic channel on the second electrode, and a membrane comprising a gas permeable polymer on the microfluidic channel, wherein the distance between the second electrode and the membrane is less than 500 microns;
an inlet for an oxidant to the first electrochemical reactor; and
an inlet for a reductant to the second electrochemical reactor.

19. The electrochemical reactor of claim 1, wherein at least two microfluidic channels are on the electrode, and the membrane is on the microfluidic channels, the membrane having a thickness from 1 micron to 2 millimeters;
wherein the microfluidic channels include:
side walls extending between the electrode and the membrane;
a distance between the side walls from 1 micron to 1 millimeter; and
a separation between the channels from 1 micron to 1 millimeter.

* * * * *